US009504275B2

(12) United States Patent
Harel et al.

(10) Patent No.: US 9,504,275 B2
(45) Date of Patent: *Nov. 29, 2016

(54) DRY STORAGE STABILIZING COMPOSITION FOR BIOLOGICAL MATERIALS

(75) Inventors: Moti Harel, Pikesville, MD (US); Qiong Tang, Columbia, MD (US)

(73) Assignee: Advanced BioNutrition Corporation, Columbia, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/208,459

(22) Filed: Aug. 12, 2011

(65) Prior Publication Data

US 2012/0039956 A1 Feb. 16, 2012

Related U.S. Application Data

(60) Provisional application No. 61/373,711, filed on Aug. 13, 2010.

(51) Int. Cl.

| | | |
|---|---|---|
| A61K 47/42 | (2006.01) | |
| A23L 1/30 | (2006.01) | |
| A01N 1/02 | (2006.01) | |
| A23L 1/00 | (2006.01) | |
| A23L 3/44 | (2006.01) | |
| A23P 1/04 | (2006.01) | |
| A61K 39/12 | (2006.01) | |
| C12N 1/04 | (2006.01) | |
| A61K 39/00 | (2006.01) | |

(52) U.S. Cl.
CPC ........... *A23L 1/3014* (2013.01); *A01N 1/0221* (2013.01); *A01N 1/0284* (2013.01); *A01N 1/0289* (2013.01); *A23K 10/18* (2016.05); *A23K 20/10* (2016.05); *A23K 20/142* (2016.05); *A23K 20/147* (2016.05); *A23K 20/163* (2016.05); *A23K 40/30* (2016.05); *A23L 1/0029* (2013.01); *A23L 3/44* (2013.01); *A23P 1/04* (2013.01); *A61K 39/12* (2013.01); *C12N 1/04* (2013.01); *A61K 2039/5252* (2013.01); *A61K 2039/542* (2013.01); *C12N 2760/16011* (2013.01); *C12N 2760/16034* (2013.01)

(58) Field of Classification Search
CPC ..... A23L 1/3014; A23L 3/44; A23L 1/0029; A23L 20/10; A61K 39/12; A61K 2039/5252; A61K 2039/542; C12N 2760/16011; C12N 2760/16034; A23K 20/163; A23K 40/30; A23K 10/18; A23K 20/147; A23K 20/142; A01N 1/0221; A01N 1/0284; A01N 1/0289
See application file for complete search history.

(56) References Cited

U.S. PATENT DOCUMENTS

| | | |
|---|---|---|
| 3,241,977 A | 3/1966 | Mitchell et al. |
| 3,897,307 A | 7/1975 | Porubcan |
| 4,337,242 A | 6/1982 | Markus et al. |
| 4,656,767 A | 4/1987 | Tarrant |
| 5,227,373 A | 7/1993 | Alexander |
| 5,262,187 A | 11/1993 | Hahn |
| 5,407,957 A | 4/1995 | Kyle |
| 5,518,918 A | 5/1996 | Barclay |
| 5,637,494 A | 6/1997 | King |
| 5,658,767 A | 8/1997 | Kyle |
| 5,715,774 A | 2/1998 | Adey |
| 5,731,006 A | 3/1998 | Akiyama |
| 5,766,520 A | 6/1998 | Bronshtein |
| 5,908,622 A | 6/1999 | Barclay |
| 5,958,455 A | 9/1999 | Roser |
| 5,968,569 A | 10/1999 | Cavadini |
| 5,981,719 A | 11/1999 | Woiszwillo |
| 6,060,050 A | 5/2000 | Brown |
| 6,187,330 B1 | 2/2001 | Wang |
| 6,190,701 B1 | 2/2001 | Roser et al. |
| 6,258,362 B1 | 7/2001 | Loudon |

(Continued)

FOREIGN PATENT DOCUMENTS

| | | |
|---|---|---|
| CL | 9312008 | 3/2008 |
| CN | 101287449 A | 10/2008 |

(Continued)

OTHER PUBLICATIONS

Ketts et al ("Citrate increases glass transition temperature of vitrified sucrose preparations," Cryobiology 48 (2004) 46 54).*

(Continued)

*Primary Examiner* — Suzanne Ziska
(74) *Attorney, Agent, or Firm* — RatnerPrestia

(57) ABSTRACT

The present invention includes compositions and drying methods for preserving sensitive bioactive materials, such as peptides, proteins, hormones, nucleic acids, antibodies, drugs vaccines, yeast, bacteria (probiotic or otherwise), viruses and/or cell suspensions, in storage. The compositions include a carbohydrates component and a glass enhancer component, wherein the carbohydrate component includes a mixture of di-, oligo- and polysaccharides and the glass enhancer includes ions of organic acid and protein hydrolysates. The composition is prepared by dispersing all the solid components in a solution and then snap-frozen to form small beads, strings or droplets. The preferred drying method of the frozen beads, strings or droplets is initiated by a short purging and structure stabilizing step of the frozen particles under a vacuum pressure of less than <2000 mTORR followed by a primary drying step under vacuum pressure of more than >2000 mTORR and at a desired temperature. During the secondary and final drying step of the material a full vacuum pressure and elevated temperature are applied, to achieve a final desirable water activity of the dry material.

24 Claims, 6 Drawing Sheets

(56) References Cited

U.S. PATENT DOCUMENTS

| | | |
|---|---|---|
| 6,267,958 B1 | 7/2001 | Andya et al. |
| 6,290,991 B1 | 9/2001 | Roser et al. |
| 6,306,345 B1 | 10/2001 | Bronshtein et al. |
| 6,331,310 B1 | 12/2001 | Roser et al. |
| 6,338,856 B1 | 1/2002 | Allen |
| 6,338,866 B1 | 1/2002 | Criggall |
| 6,451,567 B1 | 9/2002 | Barclay |
| 6,468,782 B1 | 10/2002 | Tunnacliffe et al. |
| 6,503,411 B1 | 1/2003 | Franks et al. |
| 6,509,146 B1 | 1/2003 | Bronshtein |
| 6,509,178 B1 | 1/2003 | Tanaka |
| 6,534,087 B2 | 3/2003 | Busson et al. |
| 6,537,666 B1 | 3/2003 | Bronshtein |
| 6,565,871 B2 | 5/2003 | Roser et al. |
| 6,582,941 B1 | 6/2003 | Yokochi |
| 6,586,006 B2 | 7/2003 | Roser et al. |
| 6,589,560 B2 * | 7/2003 | Foster et al. .............. 424/489 |
| 6,664,099 B1 | 12/2003 | Worrall |
| 6,716,460 B2 | 4/2004 | Abril |
| 6,726,934 B1 | 4/2004 | Prokop |
| 6,733,759 B2 | 5/2004 | Ivey et al. |
| 6,790,453 B2 | 9/2004 | Porzio et al. |
| 6,797,266 B2 | 9/2004 | Naidu |
| 6,811,792 B2 | 11/2004 | Roser et al. |
| 6,841,181 B2 | 1/2005 | Jager |
| 6,872,357 B1 | 3/2005 | Bronshtein |
| 6,884,866 B2 | 4/2005 | Bronshtein et al. |
| 6,900,173 B2 | 5/2005 | Martin |
| 6,919,172 B2 | 7/2005 | DePablo et al. |
| 6,964,771 B1 | 11/2005 | Roser et al. |
| 7,005,280 B2 | 2/2006 | Barclay |
| 7,052,719 B2 | 5/2006 | Bernstein |
| 7,056,495 B2 | 6/2006 | Roser |
| 7,122,370 B2 | 10/2006 | Porubcan |
| 7,153,472 B1 | 12/2006 | Bronshtein |
| 7,258,873 B2 | 8/2007 | Truong-Le |
| 7,282,194 B2 | 10/2007 | Sung et al. |
| 7,381,425 B1 | 6/2008 | Truong-Le |
| 7,396,548 B2 | 7/2008 | Kyle |
| 7,744,925 B2 | 6/2010 | Roser et al. |
| 7,842,310 B2 | 11/2010 | Hwang |
| 7,927,858 B2 | 4/2011 | Mayeresse |
| 7,939,105 B2 | 5/2011 | Parikh |
| 7,998,502 B2 | 8/2011 | Harel |
| 8,097,245 B2 | 1/2012 | Harel |
| 8,377,496 B2 | 2/2013 | Clinger |
| 8,460,726 B2 | 6/2013 | Harel |
| 8,834,951 B2 | 9/2014 | Harel |
| 8,968,721 B2 | 3/2015 | Harel |
| 9,044,497 B2 | 6/2015 | Harel |
| 9,072,310 B2 | 7/2015 | Harel |
| 2001/0012610 A1 | 8/2001 | Bronshtein |
| 2001/0016220 A1 | 8/2001 | Jager |
| 2002/0192202 A1 | 12/2002 | Naidu |
| 2003/0017192 A1 | 1/2003 | Kanafani |
| 2003/0022333 A1 | 1/2003 | Bronshtein |
| 2003/0165472 A1 * | 9/2003 | McGrath et al. ............ 424/93.4 |
| 2003/0190332 A1 | 10/2003 | Gilad |
| 2004/0038825 A1 | 2/2004 | Leland |
| 2004/0047881 A1 | 3/2004 | Kyle |
| 2004/0081638 A1 | 4/2004 | Kyle |
| 2004/0081699 A1 | 4/2004 | Rademacher |
| 2004/0175389 A1 | 9/2004 | Porubcan |
| 2004/0177392 A1 | 9/2004 | Barratt et al. |
| 2004/0219206 A1 | 11/2004 | Roser et al. |
| 2004/0241313 A1 | 12/2004 | Nana et al. |
| 2005/0019417 A1 | 1/2005 | Ko et al. |
| 2005/0032192 A1 | 2/2005 | Vesey |
| 2005/0079244 A1 | 4/2005 | Giffard |
| 2005/0100559 A1 | 5/2005 | Myatt et al. |
| 2005/0153018 A1 | 7/2005 | Ubbink |
| 2005/0241011 A1 | 10/2005 | Allnut et al. |
| 2005/0266069 A1 | 12/2005 | Simmons et al. |
| 2006/0008861 A1 | 1/2006 | Allnutt et al. |
| 2006/0024404 A1 | 2/2006 | Kyle |
| 2006/0120999 A1 | 6/2006 | Dhar et al. |
| 2006/0121468 A1 | 6/2006 | Allnutt et al. |
| 2006/0127453 A1 | 6/2006 | Harel |
| 2006/0130162 A1 | 6/2006 | Kyle et al. |
| 2006/0147500 A1 | 7/2006 | Klingeberg |
| 2006/0154067 A1 | 7/2006 | Cooper |
| 2006/0222694 A1 | 10/2006 | Oh |
| 2006/0258623 A1 | 11/2006 | Harel |
| 2006/0265766 A1 | 11/2006 | Kyle et al. |
| 2007/0020289 A1 | 1/2007 | Mattern |
| 2007/0031534 A1 | 2/2007 | Tsujimoto et al. |
| 2007/0082008 A1 | 4/2007 | Harel et al. |
| 2007/0122397 A1 | 5/2007 | Sanguansri |
| 2007/0207165 A1 | 9/2007 | Thiry |
| 2007/0292952 A1 | 12/2007 | Dhar et al. |
| 2008/0044081 A1 | 2/2008 | Lieb |
| 2008/0044481 A1 | 2/2008 | Harel |
| 2008/0050497 A1 * | 2/2008 | Mai et al. .............. 426/575 |
| 2008/0102132 A2 | 5/2008 | Giner |
| 2008/0131514 A1 | 6/2008 | Truong-Le et al. |
| 2008/0193546 A1 | 8/2008 | Roser et al. |
| 2008/0194504 A1 | 8/2008 | Kyle et al. |
| 2008/0221231 A1 | 9/2008 | Cooper |
| 2008/0229609 A1 | 9/2008 | Bronshtein |
| 2008/0241244 A1 | 10/2008 | Truong-Le |
| 2008/0261916 A1 | 10/2008 | Jaszberenyi |
| 2009/0155351 A1 | 6/2009 | Hejl et al. |
| 2009/0162518 A1 | 6/2009 | Clinger |
| 2009/0162521 A1 | 6/2009 | Clinger |
| 2009/0181363 A1 | 7/2009 | Dhar |
| 2009/0203592 A1 | 8/2009 | Beermann |
| 2009/0208585 A1 | 8/2009 | Roser et al. |
| 2009/0232894 A1 | 9/2009 | Chouvenc et al. |
| 2009/0238890 A1 | 9/2009 | Piechocki et al. |
| 2009/0246184 A1 * | 10/2009 | Harel et al. ............... 424/93.44 |
| 2009/0324636 A1 | 12/2009 | Piechocki et al. |
| 2010/0015177 A1 | 1/2010 | Drew |
| 2010/0047393 A1 | 2/2010 | Glas |
| 2010/0074994 A1 * | 3/2010 | Harel et al. .............. 426/61 |
| 2010/0086638 A1 | 4/2010 | Kyle et al. |
| 2010/0092521 A1 | 4/2010 | Dhar et al. |
| 2010/0120014 A1 | 5/2010 | Bronshtein |
| 2010/0120676 A1 | 5/2010 | Boehm |
| 2010/0189767 A1 | 7/2010 | Shimoni |
| 2010/0242301 A1 | 9/2010 | Rampersad |
| 2010/0297231 A1 | 11/2010 | Vehring et al. |
| 2011/0070334 A1 | 3/2011 | Rangavajla |
| 2011/0223282 A1 | 9/2011 | BergonzelliDegonda |
| 2012/0009248 A1 | 1/2012 | Truong-Le et al. |
| 2012/0039956 A1 | 2/2012 | Harel et al. |
| 2012/0040010 A1 | 2/2012 | Harel et al. |
| 2012/0114621 A1 | 5/2012 | Harel |
| 2012/0135017 A1 | 5/2012 | Harel |
| 2012/0288483 A1 | 11/2012 | Harel |
| 2012/0322663 A1 | 12/2012 | Harel |
| 2013/0287896 A1 | 10/2013 | Harel |
| 2013/0296165 A1 | 11/2013 | Harel |

FOREIGN PATENT DOCUMENTS

| | | |
|---|---|---|
| CN | 101951789 | 1/2011 |
| CN | 102186360 | 9/2011 |
| EP | 0028563 | 5/1981 |
| EP | 0259739 | 3/1988 |
| EP | 0 471 904 A1 | 2/1992 |
| EP | 1110462 | 6/2001 |
| EP | 1344458 | 9/2003 |
| GB | 1 232 057 A | 5/1971 |
| GB | 2389787 | 12/2003 |
| JP | 57114527 | 7/1982 |
| JP | 05246856 | 9/1993 |
| JP | 06-022746 | 2/1994 |
| JP | 11506467 | 6/1999 |
| JP | 11513700 | 11/1999 |
| JP | 2001505431 | 4/2001 |
| JP | 2002530321 | 9/2002 |
| JP | 2004506437 | 3/2004 |
| JP | 2004525106 | 8/2004 |
| JP | 2004528288 | 9/2004 |

(56) References Cited

FOREIGN PATENT DOCUMENTS

| | | |
|---|---|---|
| JP | 2005501268 | 1/2005 |
| JP | 2005519600 | 7/2005 |
| JP | 2005 270100 A | 10/2005 |
| JP | 2005534741 | 11/2005 |
| JP | 2007519796 | 7/2007 |
| JP | 2007522085 | 8/2007 |
| JP | 2009522280 | 6/2009 |
| JP | 2010512755 | 4/2010 |
| KR | 20050105669 | 11/2005 |
| KR | 1020050106559 | 11/2005 |
| WO | 9527721 | 10/1995 |
| WO | 9640077 | 12/1996 |
| WO | 9824882 | 6/1998 |
| WO | WO 98/24327 | 6/1998 |
| WO | 0032064 | 6/2000 |
| WO | WO 01/12779 | 2/2001 |
| WO | 0136590 | 5/2001 |
| WO | WO 02/15720 | 2/2002 |
| WO | 02058735 | 8/2002 |
| WO | WO 02/061111 | 8/2002 |
| WO | WO 02/076391 | 10/2002 |
| WO | 03086454 | 10/2003 |
| WO | 03088755 | 10/2003 |
| WO | WO 03/089579 | 10/2003 |
| WO | WO03103692 | 12/2003 |
| WO | 2004022728 | 3/2004 |
| WO | 2004024177 | 3/2004 |
| WO | WO 2004/039417 A2 | 5/2004 |
| WO | WO2004043139 | 5/2004 |
| WO | 2004080196 | 9/2004 |
| WO | WO2004091307 | 10/2004 |
| WO | 2004112776 | 12/2004 |
| WO | WO 2004/112767 | 12/2004 |
| WO | 2005030229 | 4/2005 |
| WO | WO 2005/060937 A1 | 7/2005 |
| WO | WO 2005/084646 | 9/2005 |
| WO | WO 2005/105978 | 11/2005 |
| WO | 2005115341 | 12/2005 |
| WO | 2005117962 | 12/2005 |
| WO | 2006085082 | 8/2006 |
| WO | WO 2006/122299 | 11/2006 |
| WO | 2007035455 | 3/2007 |
| WO | WO 2007/038926 A1 | 4/2007 |
| WO | WO2007067207 | 6/2007 |
| WO | 2007084059 | 7/2007 |
| WO | 2007084500 | 7/2007 |
| WO | WO 2007/075988 | 7/2007 |
| WO | WO 2007/079147 | 7/2007 |
| WO | 2007117511 | 10/2007 |
| WO | 2007136553 | 11/2007 |
| WO | 2008016214 | 2/2008 |
| WO | 2008056983 | 5/2008 |
| WO | WO 2008/076975 | 6/2008 |
| WO | 2009002481 | 12/2008 |
| WO | WO2009140327 | 11/2009 |
| WO | WO 2010/002418 A2 | 1/2010 |
| WO | 2010046321 | 4/2010 |
| WO | WO2010111347 | 9/2010 |
| WO | WO2010118188 | 10/2010 |
| WO | WO2010118205 | 10/2010 |
| WO | WO 2010/135495 A2 | 11/2010 |
| WO | WO2010138522 | 12/2010 |
| WO | WO2011094469 | 8/2011 |

OTHER PUBLICATIONS

Zarate et al ("Viability and biological properties of probiotic vaginal lactobacilli after lyophilization and refrigerated storage into gelatin capsules," Process Biochemistry 41 (2006) 1779-1785).*
Morgan, C.A., Herman, N., White, P.A., Vesey, G., 2006, Preservation of micro-organisms by drying; a review. *J. Microbiol. Methods.* 66(2):183-93.
Capela, P., Hay, T. K. C., & Shah, N. P., 2006, Effect of cryoprotectants, prebiotics and microencapsulation on survival of probiotic organisms in yoghurt and freeze-dried yoghurt. *Food Research International*, 39(3) 203-211).
Annear, 1962, The Preservation of *Leptospires* by Drying From the Liquid State, *J. Gen. Microbiol.*, 27:341-343.
Crowe, J.F., Carpenter, J.F. and Crowe, L.M., 1998, The Role of Vitrification in Anhydrobiosis. *Annu. Rev. Physiol.* 60:73-103.
Crowe, J. H., Crowe., L. M., and Mouriadian, R., 1983, *Cryobiology*, 20, 346-356.
M. Le Meste, et al., 2002, Glass Transition and Food Technology: A Critical Appraisal, *Journal of Food Science*, 67:2444-2458.
Sanchez et al., 1999, *Intl. J. Pharm.* 185, 255-266.
Esquisabel et al., 1997, *J. Microencapsulation*, 14, 627-638.
Kets et al., 2004. Citrate increases glass transition temperature of vitrified sucrose preparations, *Cryobiology*, 48:46-54.
De Giulio, et al., "Use of alginate and cryo-protective sugars to improve the viability of lactic acid and bacteria after freezing and freeze-drying",World Journal of Microbiology and Biotechnology, Kluwer Academic Publishers, DO, vol. 21, No. 5, Jul. 1, 2005, pp. 739-746.
Kearney, et al., "Enhancing the Viability of Lactobacillus plantarum Inoculum by Immobilizing the Cells in Calcium-Algiinate Beads Incorporation Cryoprotectants", Applied and Environmental Microbiology, vol. 56, No. 10, Oct. 1990, pp. 3112-3116.
Selmer-Olsen, et al., "Survival of Lactobacillus helveticus entrapped in Ca-alginate in relation to water content, storage and rehydration", Journal of Industrial Microbiology & Biotechnology, vol. 23, 1999, pp. 79-85.
Chen, et al., "Beneficial Effect of Intracellular Trehalsose on the Membrane Integrity of Dried Mammalian Cells", Cryobiology vol. 43, pp. 168-181, 2001.
Crowe et al., "Anhydrobiosis: A Strategy for Survival", Adv. Space Res vol. 12, No. 4, pp. 239-247, 1992.
Favaro-Trindade et al., "Microencapsulation of L. acidophilus (La-05) and B. lactis (Bb-12) and evaluation of their survival at the pH values of the stomach and in bile", J. Microencapsulation, vol. 19, pp. 485-494, 2002.
Sutas et al., "Probiotics: effects on immunity", Am J Clin Nutr. 73, pp. 444S-450S, 2001.
Kailasapathy et al., "Survival and therapeutic potential of probiotic organisms with reference to *Lactobacillus acidophilus* and *Bifidobacterium*", spp. Immunology Cell Biology, 78, pp. 80-88, 2000.
Krallish et al., "Effect of xylitol and trehalose on dry resistance of yeasts", Appl. Microbiol Biotechnol. 47, pp. 447-451, 1997.
Liao et al., "Protective Mechanism of Stabilizing Excipients against Dehydration in the Freeze-Drying of Proteins", Pharmaceutical Research, vol. 19, No. 12, pp. 1864-61, 2002.
Linders et al., "Effect of Added Carbohydrates on Membrane Phase Behavior and Survival of Dried Lactobacillus plantarum", Cryobiology 35, pp. 31-40, 1997.
Marteau et al., "Protection from gastrointestinal diseases with the use of probiotics", Am J Clin Nutr. 73, pp. 430S-436S, 2001.
Perdigon et al, "Lactic Acid Bacteria and their Effect on the Immune System", Curr Issues Intest Microbiol. 2, pp. 27-42, 2001.
Qiu et al., "Permeability of the infective juveniles of Steinernema carpocapsae to glycerol during osmotic dehydration and its effect on biochemical adaptation and energy metabolism", Comparative Biochemistry & Physiology, Part B, vol. 125, pp. 411-419, 2000.
Shah, "Probiotic bacteria: Selective Enumeration and Survival in Dairy Foods", J. Dairy Sci 83, pp. 894-907, 2000.
Examination Report issued in related Chilean Application No. 01984-2011, dated Jan. 24, 2014.
Japanese Office Action issued in related Japanese Application No. 2013-524242, dated Jan. 21, 2014.
Chinese Search Report dated May 26, 2014 for application No. 201180039219.7 filed Aug. 12, 2011.
Abdelwahed et al., Advanced Drug Delivery Reviews, 58:1688-713 (2006).
Chen et al., China Tropical Medicine, 7(4):654-55 (2007) (with partial English translation).
Desai et al., Pharmaceutical Research, 13(12):1838-45 (1996).

(56) References Cited

OTHER PUBLICATIONS

First Office Action with a Search Report issued by the State Intellectual Property Office of the People's Republic of China on May 22, 2013 for Chinese Application No. 201180007562.3.
International Preliminary Report on Patentability for PCT International Application No. PCT/US2011/022821 dated Jul. 31, 2012.
Second Office Action issued by the State Intellectual Property Office of the People's Republic of China Feb. 8, 2014 in corresponding Chinese Application No. 201180007562.3, including a Search Report (with English translation).
Supplementary European Search Report for European Appln No. 11737688.9 dated Sep. 18, 2013.
Tobar et al., Oral Vaccination of Atlantic Salmon *Salmo salar* against Salmonid *Rickettsial septicaemia* (SRS), abstract, World Aquaculture Society's 2008 annual international conference (May 19-23, 2008).
Tobar at al., Oral Vaccination of Atlantic Salmon *Salmo salar* against Salmon *Rickettsial Septicaemia* presentation, World Aquaculture Society's 2008 annual international conference (May 19-23, 2008).
Wong, Recent Patents on Drug Delivery & Formation 3:1720-23 (2009).
Anal et al. "Recent advances in microencapsulation of probiotics for industrial applications and targeted delivery." Trends in Food Science and Technology, vol. 18, No. 5, Apr. 29, 2007, pp. 240-251.
Anderson, J.W., Johnstone, B.M. and Remley, D.T. (1999). Breast-feeding and cognitive development: a meta-analysis. Am J Clin Nutr, 70, 525-35.
Bazan, N.G. and Rodriguez de Truco E.B. (1994). Review: pharmacological manipulation of docosahexaerioic-phospholipid biosynthesis in photorecptor cells: implications in retinal degeneration. J. Ocul Pharmacol. 10, 591-604.
Bazan, N.G. and Scott, B.L. (1990). Dietary omega-3 fatty acids and accumulation of docosahexaenoic acid in rod photoreceptor cells of the retina and at synapses. Ups J Med Sci Suppl, 48, 97-107.
Behrens, P. and Kyle, D. (1996). Microalgae as a source of fatty acids. J Food Sci, 3, 259-272.
Bergogne et al., Molecular Crystals and Liquid Crystals, 354: 79-89 (2000).
Boswell KDB, Gladue R, Prima B, Kyle DJ (1992) SCO production of fermentive microalgae In: Kyle DJ. Ratledge C (eds) Industrial Applications of Single Cell Oils. American Oil Chemists Society, Champaign, IL., pp. 274-286.
Canadian Office Action mailed Apr. 6, 2011 in Canadian Application No. 2,673,120.
Crawford, M.A., Costeloe, K., Ghebresmeskai, K. and Phyiactos, A. (1998). The inadequacy of the essential fatty acid content of present preterm feeds [published erratum appears in Eur J. Pediatr Feb. 1998; 157(2):160]. Eur. J Pediatr, 157 Suppl 1, S23-7.
Grinstead G, Tokach M, Dritz, S, Goodband R, Nelssen J (2000) Effects of Spirulina platensis on growth performance of weanling pigs. Animal Feed Sci Technol 83:237-247.
He ML, Hollwich W, Rambeck WA (2002) Supplementation of algae to the diet of pigs: a new possibility to improve the iodine content in the meat. J Animal Physiol Animal Nutri 86:97-104.
Hincha, D., et al., "Protection of liposomes against fusion during drying of oligosaccharides is not predicted by the calorimetric glass transition temperatures of the dry sugars." European Biophysics Journal, 37 (2008) 503-508.
Hughes, V.X. and Hillier, S.L. (1990). "Microbiologic characteristics of Lactobacillus products used for colonization of the vagina." Obstet Gynecol. 75:244-248.
Ikernoto, A., Kobayashi, T., Watanabe, S. and Okuyama, H. (1997). Membrane fatty acid modifications of PC12 cells by arachidonate or docosahexaenoate affect neurite outgrowth but not norepinephrine release. Neurochem Res, 22, 671-8.
International Search Report for International Application No. PCT/US2006/49434 dated Sep. 26, 2007.
International Search Report for International Application No. PCT/US2007/087771 mailed May 16, 2008.
Japanese Office Action for Japanese Patent Application No. 2008-548729, mailed Jul. 23, 2012 (with English translation).
Japanese Office Action mailed Aug. 1, 2014 in Japanese Application No. 2012-513183, with translation (with English Translation).
Krasaekoopt et al. "Evaluation of encapsulation techniques of probiotics for yoghurt." International Dairy Journal 13, 2003. pp. 3-13.
Martinez, M. (1990), Severe deficiency of docosahexaenoic acid in peroxisomal disorders: a defect of delta 4 desaturation. Neurology, 40, 1292-8.
Mazur et al., Hydration of Sodium Alginate in Aqueous Solution, Macromolecules, (2014) 47: 771-776.
New Zealand Examination Report dated May 18, 2012 in New Zealand Application No. 597053.
Niness, Inulin and Olgifructose: What are they?., J. Nutr. 129, 1999, pp. 1402S-1406S.
Office Action dated Mar. 21, 2014 in Russian patent application No. 2011151788/10(077759) (with English translation).
Office Action for Patent Application JP 2009-541634 mailed Jun. 25, 2012 (with English translation).
Office Action mailed Aug. 6, 2014 in Russion Application No. 2011151788/10 (077759) (with English translation).
Schwab, C., et al., "Influence of oligosaccharides on the viability and membrane properties of lactobacillus reuteri TMW1.106 during freeze-drying," Cryobiology, 55 (2007) 108-114.
Shin et al., Growth and Viability of Commercial *Bifidobacterium* spp in Skim Milk containing oligosaccharides and Inulin, Journal of Food Science, 2000, vol. 65, No. 5, pp. 884-887.
Stordy, BJ. (1995). Benefit of docosahexaenoic acid supplements to dark adaptation in dyslexics. Lancet, 346 (8971): 385.
Substantive Examination Adverse Report mailed Aug. 29, 2014 in Malaysian Application No. PI 2011005733.
Supplementary European Search report in European Application No. EP 10781100.2-2405 dated Oct. 9, 2012.
Xu, L.Z., Sanchez, R., Sali, A. and Heintz, N, (1996). Ligand specificity of brain lipid-binding protein. J Biol Chem, 271, 24711-9.
Singapore Search Report and Written Opinion mailed Sep. 9, 2015 for Application No. 11201405478V.
Office Action mailed May 22, 2015 in U.S. Appl. No. 13/849,941.
Mexican Office Action mailed Jul. 20, 2015 in Mexican Application No. MX/a/2012/008795.
New Zealand Office Action mailed Jun. 24, 2015 in New Zealand Application No. 628912.
Russian Office Action mailed Jul. 21, 2015 in Russian Application No. 2013110833/13(016008).
Benedict, R.G. et al., "Preservation of Microorganisms by Freeze-Drying I. Cell Supernatant, Naylor-Smith Solution, and Salts of Various Acids as Stabilizers for Serratia marcascens," Appl. Microbiol. 1958, vol. 6, No. 6, pp. 401-407.
Canadian Office Action mailed Oct. 10, 2014 in Canadian Application No. 2,785,815.
European Office Action for Application No. 10 781 100.2-1403 dated Oct. 17, 2014.
Extended European Search Report for European Application No. 11817090.1-1358 dated Jun. 16, 2014.
International Preliminary Report on Patentability and Written Opinion for PCT International Application No. PCT/US2013/033505 issued Sep. 23, 2014.
International Search Report for International Application No. PCT/US2010/036098 ailed Feb. 14, 2011.
International Search Report for International Application No. PCT/US2011/022821 mailed Oct. 25, 2011.
Maltrin M100 Maltodrexin, 2006, XP055120984, Internet retrieves from the Internet: URL: http://www.tpipremixes.com/productpdfs/Maltodextrin.pdf, retrieved on Jun. 2, 2014.
Notice of Allowance mailed Oct. 27, 2014 in U.S. Appl. No. 13/459,408.
Perry, Stephen F, "Freeze-Drying and Cryopreservation of Bacteria," Molecular Biotechnology, 1998, vol. 9, No. 1, pp. 59-64.
Sucrose, Sucrose Structure, Webpage from Virtual Chembook, Elmhurst College, Charles E. Ophardt, c. 2003.

(56) References Cited

OTHER PUBLICATIONS

Notice of Allowance mailed Jan. 15, 2015 in U.S. Appl. No. 13/911,636.
Office Action mailed Jan. 14, 2015 in U.S. Appl. No. 13/321,708.
Russian Office Action mailed Dec. 18, 2014 in Application No. 2011151788/10(077759).
Australian Patent Examination Report dated Jan. 23, 2015 in Patent Application No. 2010254235.
Entire patent prosecution history of U.S. Appl. No. 12/519,860, filed Dec. 2, 2009, entitled, "Dry Food Product Containing Live Probiotic," now U.S. Pat. No. 8,460,726 at Notice of Allowance dated Feb. 12, 2013.
Entire patent prosecution history of U.S. Appl. No. 12/519,860, filed Dec. 2, 2009, entitled, "Dry Food Product Containing Live Probiotic," now U.S. Pat. No. 8,460,726 at Response after Final dated Jan. 7, 2013.
Entire patent prosecution history of U.S. Appl. No. 12/519,860, filed Dec. 2, 2009, entitled, "Dry Food Product Containing Live Probiotic," now U.S. Pat. No. 8,460,726 at Interview Summary dated Dec. 21, 2012.
Entire patent prosecution history of U.S. Appl. No. 12/519,860, filed Dec. 2, 2009, entitled, "Dry Food Product Containing Live Probiotic," now U.S. Pat. No. 8,460,726 at Final Office Action dated Nov. 6, 2012.
Entire patent prosecution history of U.S. Appl. No. 12/519,860, filed Dec. 2, 2009; entitled, "Dry Food Product Containing Live Probiotic," now U.S. Pat. No. 8,460,726 at Interview Summary dated Oct. 19, 2012.
Entire patent prosecution history of U.S. Appl. No. 12/519,860, filed Dec. 2, 2009, entitled; "Dry Food Product Containing Live Probiotic," now U.S. Pat. No. 8,460,726 at Applicant summary of interview with examiner dated Oct. 18, 2012.
Entire patent prosecution history of U.S. Appl. No. 12/519,860, filed Dec. 2, 2009, entitled, "Dry Food Product Containing Live Probiotic," now U.S. Pat. No. 8,460,726 at Response dated Sep. 10, 2012.
Entire patent prosecution history of U.S. Appl. No. 12/519,860, filed Dec. 2, 2009, entitled, "Dry Food Product Containing Live Probiotic," now U.S. Pat. No. 8,460,726 at Non-Final Office Action dated Jun. 8, 2012.
Entire patent prosecution history of U.S. Appl. No. 12/519,860, filed Dec. 2, 2009, entitled, "Dry Food Product Containing Live Probiotic," now U.S. Pat. No. 8,460,726 at Advisory Action dated Feb. 14, 2012.
Entire patent prosecution history of U.S. Appl. No. 12/519,860, filed Dec. 2, 2009, entitled, "Dry Food Product Containing Live Probiotic," now U.S. Pat. No. 8,460,726 at Response dated Jan. 31, 2012.
Entire patent prosecution history of U.S. Appl. No. 12/519,860, filed Dec. 2, 2009, entitled, "Dry Food Product Containing Live Probiotic," now U.S. Pat. No. 8,460,726 at Final Office Action dated Nov. 9, 2011.
Entire patent prosecution history of U.S. Appl. No. 12/519,860, filed Dec. 2, 2009, entitled, "Dry Food Product Containing Live Probiotic," now U.S. Pat. No. 8,460,726 at Response dated Sep. 23, 2011.
Entire patent prosecution history of U.S. Appl. No. 12/519,860, filed Dec. 2, 2009, entitled, "Dry Food Product Containing Live Probiotic," now U.S. Pat. No. 8,460,726 at Non-Final Office Action dated Sep. 2, 2011.
Entire prosecution history of U.S. Appl. No. 12/159,407, filed Nov. 21, 2008, entitled, "Delivery Vehicle for Probiotic Bacteria Comprising a Dry Matrix of Polysaccharides, Saccharides and Polyols in a Glass Form and Methods of Making Same," now U.S. Pat. No. 8,097,245 at Notice of Allowance dated Oct. 24, 2011.
Entire prosecution history of U.S. Appl. No. 12/159,407, filed Nov. 21, 2008, entitled, "Delivery Vehicle for Probiotic Bacteria Comprising a Dry Matrix of Polysaccharides, Saccharides and Polyols in a Glass Form and Methods of Making Same," now U.S. Pat. No. 8,097,245 at Response filed Aug. 6, 2011.
Entire prosecution history of U.S. Appl. No. 12/159,407, filed Nov. 21, 2008, entitled, "Delivery Vehicle for Probiotic Bacteria Comprising a Dry Matrix of Polysaccharides, Saccharides and Polyols in a Glass Form and Methods of Making Same," now U.S. Pat. No. 8,097,245 at Restriction Requirement dated Jul. 6, 2011.
Entire prosecution history of U.S. Appl. No. 13/321,708, filed Feb. 6, 2012, entitled, "Stable Dry Powder Composition Comprising Biologically Active Microorganisms and/or Bioactive Materials and Methods of Making" at Response dated Sep. 9, 2014.
Entire prosecution history of U.S. Appl. No. 13/321,708, filed Feb. 6, 2012, entitled, "Stable Dry Powder Composition Comprising Biologically Active Microorganisms and/or Bioactive Materials and Methods of Making" at Non-Final Office Action dated May 9, 2014.
Entire prosecution history of U.S. Appl. No. 13/321,708, filed Feb. 6, 2012, entitled, "Stable Dry Powder Composition Comprising Biologically Active Microorganisms and/or Bioactive Materials and Methods of Making" at Response dated Mar. 18, 2014.
Entire prosecution history of U.S. Appl. No. 13/321,708, filed Feb. 6, 2012, entitled, "Stable Dry Powder Composition Comprising Biologically Active Microorganisms and/or Bioactive Materials and Methods of Making" at Final Office Action dated Jan. 15, 2014.
Entire prosecution history of U.S. Appl. No. 13/321,708, filed Feb. 6, 2012, entitled, "Stable Dry Powder Composition Comprising Biologically Active Microorganisms and/or Bioactive Materials and Methods of Making" at Response dated Oct. 9, 2013.
Entire prosecution history of U.S. Appl. No. 13/321,708, filed Feb. 6, 2012, entitled, "Stable Dry Powder Composition Comprising Biologically Active Microorganisms and/or Bioactive Materials and Methods of Making" at Non-Final Office Action dated Jul. 11, 2013.
Entire prosecution history of U.S. Appl. No. 13/321,708, filed Feb. 6, 2012, entitled, "Stable Dry Powder Composition Comprising Biologically Active Microorganisms and/or Bioactive Materials and Methods of Making" at Response dated May 1, 2013.
Entire prosecution history of U.S. Appl. No. 13/321,708, filed Feb. 6, 2012, entitled, "Stable Dry Powder Composition Comprising Biologically Active Microorganisms and/or Bioactive Materials and Methods of Making" at Restriction Requirement dated Mar. 4, 2013.
Entire prosecution history of U.S. Appl. No. 13/351,343, filed Jan. 17, 2012, entitled, "Delivery Vehicle for Probiotic Bacteria Comprising a Dry Matrix of Polysaccharides, Saccharides and Polyols in a Glass Form and Methods of Making Same" at Notice of Allowance and Interview Summary dated Jun. 26, 2014.
Entire prosecution history of U.S. Appl. No. 13/351,343, filed Jan. 17, 2012, entitled, "Delivery Vehicle for Probiotic Bacteria Comprising a Dry Matrix of Polysaccharides, Saccharides and Polyols in a Glass Form and Methods of Making Same" at Advisory Action dated Apr. 1, 2013.
Entire prosecution history of U.S. Appl. No. 13/351,343, filed Jan. 17, 2012, entitled, "Delivery Vehicle for Probiotic Bacteria Comprising a Dry Matrix of Polysaccharides, Saccharides and Polyols in a Glass Form and Methods of Making Same" at Response dated Mar. 20, 2013.
Entire prosecution history of U.S. Appl. No. 13/351,343, filed Jan. 17, 2012, entitled, "Delivery Vehicle for Probiotic Bacteria Comprising a Dry Matrix of Polysaccharides, Saccharides and Polyols in a Glass Form and Methods of Making Same" at Final Office Action dated Jan. 23, 2013.
Entire prosecution history of U.S. Appl. No. 13/351,343, filed Jan. 17, 2012, entitled, "Delivery Vehicle for Probiotic Bacteria Comprising a Dry Matrix of Polysaccharides, Saccharides and Polyols in a Glass Form and Methods of Making Same" at Response dated Nov. 20, 2012.
Entire prosecution history of U.S. Appl. No. 13/351,343, filed Jan. 17, 2012, entitled, "Delivery Vehicle for Probiotic Bacteria Comprising a Dry Matrix of Polysaccharides, Saccharides and Polyols in a Glass Form and Methods of Making Same" at Non-Final Office Action dated Sep. 6, 2012.
Entire prosecution history of U.S. Appl. No. 13/351,343, filed Jan. 17, 2012, entitled, "Delivery Vehicle for Probiotic Bacteria Comprising a Dry Matrix of Polysaccharides, Saccharides and Polyols in a Glass Form and Methods of Making Same" at Response filed Jul. 11, 2012.

(56) References Cited

OTHER PUBLICATIONS

Entire prosecution history of U.S. Appl. No. 13/351,343, filed Jan. 17, 2012, entitled, "Delivery Vehicle for Probiotic Bacteria Comprising a Dry Matrix of Polysaccharides, Saccharides and Polyols in a Glass Form and Methods of Making Same" at Restriction Requirement dated Jul. 2, 2012.
Entire prosecution history of U.S. Appl. No. 13/378,106, filed Mar. 29, 2012, entitled, "Dry Glassy Composition Comprising a Bioactive Material," now U.S. Pat. No. 8,834,951 at Notice of Allowance dated May 9, 2014.
Entire prosecution history of U.S. Appl. No. 13/378,106, filed Mar. 29, 2012, entitled, "Dry Glassy Composition Comprising a Bioactive Material," now U.S. Pat. No. 8,834,951 at Response dated Apr. 10, 2014.
Entire prosecution history of U.S. Appl. No. 13/378,106, filed Mar. 29, 2012, entitled, "Dry Glassy Composition Comprising a Bioactive Material," now U.S. Pat. No. 8,834,951 at Interview Summary dated Apr. 8, 2014.
Entire prosecution history of U.S. Appl. No. 13/378,106, filed Mar. 29, 2012, entitled, "Dry Glassy Composition Comprising a Bioactive Material," now U.S. Pat. No. 8,834,951 at Advisory Action dated Mar. 18, 2014.
Entire prosecution history of U.S. Appl. No. 13/378,106, filed Mar. 29, 2012, entitled, "Dry Glassy Composition Comprising a Bioactive Material," now U.S. Pat. No. 8,834,951 at Response dated Mar. 10, 2014.
Entire prosecution history of U.S. Appl. No. 13/378,106, filed Mar. 29, 2012, entitled, "Dry Glassy Composition Comprising a Bioactive Material," now U.S. Pat. No. 8,834,951 at Final Office Action dated Jan. 10, 2014.
Entire prosecution history of U.S. Appl. No. 13/378,106, filed Mar. 29, 2012, entitled, "Dry Glassy Composition Comprising a Bioactive Material," now U.S. Pat. No. 8,834,951 at Resonse dated Sep. 9, 2013.
Entire prosecution history of U.S. Appl. No. 13/378,106, filed Mar. 29, 2012, entitled, "Dry Glassy Composition Comprising a Bioactive Material," now U.S. Pat. No. 8,834,951 at Non-Final Office Action dated Jun. 10, 2013.
Entire prosecution history of U.S. Appl. No. 13/459,408, filed Apr. 30, 2012, entitled, "Delivery Vehicle for Probiotic Bacteria Comprising a Dry Matrix of Polysaccharides, Saccharides and Polyols in a Glass Form and Methods of Making Same" at Notice of Allowance and Interview Summary dated Oct. 27, 2014.
Entire prosecution history of U.S. Appl. No. 13/459,408, filed Apr. 30, 2012, entitled, "Delivery Vehicle for Probiotic Bacteria Comprising a Dry Matrix of Polysaccharides, Saccharides and Polyols in a Glass Form and Methods of Making Same" at Supplemental Response dated Oct. 9, 2014.
Entire prosecution history of U.S. Appl. No. 13/459,408, filed Apr. 30, 2012, entitled, "Delivery Vehicle for Probiotic Bacteria Comprising a Dry Matrix of Polysaccharides, Saccharides and Polyols in a Glass Form and Methods of Making Same" at Response dated Aug. 21, 2014.
Entire prosecution history of U.S. Appl. No. 13/459,408, filed Apr. 30, 2012, entitled, "Delivery Vehicle for Probiotic Bacteria Comprising a Dry Matrix of Polysaccharides, Saccharides and Polyols in a Glass Form and Methods of Making Same" at Non-Final Office Action dated Jul. 24, 2014.
Entire prosecution history of U.S. Appl. No. 13/459,408, filed Apr. 30, 2012, entitled, "Delivery Vehicle for Probiotic Bacteria Comprising a Dry Matrix of Polysaccharides, Saccharides and Polyols in a Glass Form and Methods of Making Same" at Response filed Jun. 19, 2014.
Entire prosecution history of U.S. Appl. No. 13/459,408, filed Apr. 30, 2012, entitled, "Delivery Vehicle for Probiotic Bacteria Comprising a Dry Matrix of Polysaccharides, Saccharides and Polyols in a Glass Form and Methods of Making Same" at Restriction Requirement dated Jun. 12, 2014.
Entire prosecution history of U.S. Appl. No. 13/849,941, filed Mar. 25, 2013, entitled Stablizing Composition for Biological Materials at Non-Final Office Action dated Sep. 2, 2014.
Entire prosecution history of U.S. Appl. No. 13/849,941, filed Mar. 25, 2013, entitled Stablizing Composition for Biological Materials at Response filed May 13, 2014.
Entire prosecution history of U.S. Appl. No. 13/849,941, filed Mar. 25, 2013, entitled Stablizing Composition for Biological Materials at Restriction Requirement dated Mar. 13, 2014.
Entire prosecution history of U.S. Appl. No. 13/911,636, filed Jun. 6, 2013, entitled, "Dry Food Product Containing Live Probiotic" at Notice of Allowance dated May 27, 2014.
Entire prosecution history of U.S. Appl. No. 13/911,636, filed Jun. 6, 2013, entitled, "Dry Food Product Containing Live Probiotic" at Response dated Mar. 3, 2014.
Entire prosecution history of U.S. Appl. No. 13/911,636, filed Jun. 6, 2013, entitled, "Dry Food Product Containing Live Probiotic" at Non-Final Office Action dated Oct. 3, 2013.
Japanese Office Action issued Mar. 2, 2015 in Japanese Application No. 2012-551295.
Chinese Office Action mailed Mar. 2, 2015 in Chinese Application No. 201180007562.3.
Japanese Office Action mailed Sep. 15, 2015 for Japanese Application No. 2012-513183, including English translation.
Substantive Examination Adverse Report mailed Jun. 30, 2015 in Malaysian Application No. PI 2011005733.
Office Action mailed Jun. 30, 2015 in Vietnamese Application No. 1-2011-03487.
Extended European Search Report for European Application No. 13764138.7-1460 dated Apr. 9, 2015.
Japanese Office Action issued Mar. 31, 2015 in Japanese Application No. 2012-513183.
Canadian Office Action dated Mar. 10, 2016 for Canadian Application No. 2,763,074.
Chinese Office Action dated Feb. 26, 2016 for Chinese Application No. 201380015928.0 with translation.
Chinese Search Report dated Feb. 23, 2016 for Chinese Application No. 2013800115928.0 with translation.
Aral, C. et al., "Alternative approach to the preparation of chitosan beads," International Journal of Pharmaceutics 168 (1998) 9-15.
Bodmeier, R., et al., "Preparation and evaluation of drug-containing chitosan beads," Drug Development and Industrial Pharmacy, 15(9), 1989, 1475-1494.
Bradford, M., "A rapid and sensitive method for the quantitation of microgram quantities of protein utilizing the principle of protein-dye binding," Analytical biochemistry 72 (1976) 248-254.
Calvo, P., et al., "Novel hydrophilic chitosan-polyethylene oxide nanoparticles as protein carriers," Journal of Applied Polymer Science, 63 (1997) 125-132.
Canadian Office Action mailed Sep. 8, 2015 for Canadian Application No. 2,785,815.
Chopra, S. et al., 2006. Advances and potential applications of chitosan derivatives as mucoadhesive biomaterials in modern drug delivery, J. Pharm. Pharmacol. 58(8) 1021-1032.
Deng, J.M., Leong, K.W., 2006. Natural polymers for gene delivery and tissue engineering. Adv. Drug Deliv. Rev. 58(4), 487-499.
Davis, S.S., 2006. The use of soluble polymers and polymer microparticles to provide improved vaccine responses after parenteral and mucosal delivery, Vaccine 24(2), 7-10.
Entire patent prosecution history of U.S. Appl. No. 13/260,561, filed Nov. 2, 2011, entitled, "Microparticulated vaccines for the Oral or Nasal Vaccination and Boostering of Animals Including Fish."
European Office Action mailed Nov. 6, 2015 for European Application No. 11817090.1
Examination Report on Patent Application for Chilean Application No. 759-09 dated Mar. 27, 2009.
Huang, Y.C., et al., "Optimizing formulation factors in preparing chitosan microparticles by spray-drying method," Journal of Microencapsulation, vol. 20, No. 2 (2003) 247-260.
International Search Report for Application No. PCT/US2010/028767 dated Dec. 23, 2010.

(56) References Cited

OTHER PUBLICATIONS

Kang, M.L. et al., Pluronic F127 enhances the effect as an adjuvant of chitosan microspheres in the intranasal delivery of Bordetella bronchiseptica antigens containing dermonecrotoxin. Vaccine 25(23), 4602-4610.
Kim, T.J., et al., 2007. Stimulation of mucosal and systemic antibody responses against recombinant transferrin-binding protein B of Actinobacillus pleuropneumoniae with chitosan after tracheal administration in piglets. J. Vet. Med. Sci. 69(5), 535-539.
Li, X., et al., "Preparation of alginate coated chitosan microparticles for vaccine delivery," BMC Biotechnology 8:89 (2008).
Malik, D.K., et al., 2007. Recent advances in protein and peptide drug delivery systems . . . Curr. Drug Deliv. 4(2), 141-151.
Panos, I., et al., "New drug delivery systems based on chitosan," Current Drug Discovery Technologies, 5 (2008) 333-341.
Rege, P., et al., "Spray-dried chitinosans Part I: preparation and characterization," International Journal of Pharmaceutics 252 (2003) 41-51.
Shiraishi, S., et al., "Controlled release of indomethacin by chitosan-polyelectrolyte complex: optimization and in vivo/in vitro evaluation," Journal of Controlled Release 25 (1993) 217-225.
Shu, X., et al., "A novel approach to prepare tripolyphosphate/chitosan complex beads for controlled release drug delivery," International Journal of Pharmaceutics 201 (2000) 51-58.
Tobar et al., Oral vaccination of Atlantic Salmo salar against Salmon *Rickettsial Septicaemia*, World Aquaculture Society's 2008 annual international conference (May 19-23, 2008).
van der Lubben, I.M., et al., 2001. Chitosan for mucosal vaccination. Advanced Drug Delivery Reviews 52 (2), 139-144.
van der Lubben, I.M., et al., 2001. Chitosan microparticles for oral vaccination: preparation, characterization and preliminary in vivo uptake studies in murine Payer's patches. Biomaterials 22(7), 687-694.
Zhou, S., et al., "Poly-D, L-lactide-co-poly(ethylene glycol) microspheres as potential vaccine delivery systems," Journal of Controlled Release 86 (2003) 195-205.
Non Final Office Action mailed Jan. 12, 2016 for U.S. Appl. No. 14/479,791.
Canadian Office Action mailed Dec. 8, 2015 for Canadian Application No. 2,756,883.
Chinese Reexamination Report dated Dec. 23, 2015 for Chinese Application No. 201080029392.4 with translation.
Non Final Office Action dated Jan. 22, 2016 for U.S. Appl. No. 13/321,708.
Non Final Office Action mailed Feb. 3, 2016 for U.S. Appl. No. 14/456,130.
Final Office Action mailed Feb. 3, 2016 for U.S. Appl. No. 13/849,941.
Philippine Office Action dated Jan. 14, 2016 for Philippine Application No. 1-2011-502445.
Substantive Examination Adverse Report mailed Sep. 15, 2015 in Malaysian Application No. PI 2013000306.
Japanese Office Action issued Oct. 7, 2015 in Japanese Application No. 2012-551295, including English translation.
Chinese Office Action dated Apr. 1, 2016 for Chinese Application No. 201410326898.1 with translation.
Philippines Substantive Examination Report dated Apr. 15, 2016 for Philippines Application No. 1-2012-501410.
Final Office Action for U.S. Appl. No. 13/260,661, mailed Jun. 1, 2016, 48 pages.
Miao, "Effect of disaccharides on survival during storage of freeze dried probiotics.", Dairy Scieince and Technology 88.1, 2008, pp. 19-30.
Notice of Allowance for U.S. Appl. No. 13/848,941, mailed Jun. 20, 2016, 16 pages.
Santivarangkna, et al., "Role of Glassy State on Stabilities of /freeze-Dried Probiotics.", Journal of Food Science, vol. 76, No. 8, 2011, pp. 152-156.
Non Final Office Action for U.S. Appl. No. 14/644,248, mailed Jul. 15, 2016, 58 pages.
Final Office Action for U.S. Appl. No. 13/321,708, mailed Aug. 5, 2016, 30 pages.
European Office Action for European Application No. 10756894.1, dated Jun. 22, 2016, 5 pages.
Notification of Reexamination of Chinese Application No. 201080029392.4, dated Jul. 13, 2016, 10 pages.
European Examination Report for EP Application No. 11817090.1, dated Jul. 15, 2016, 6 pages.
Indonesian Examination Report for Indonesian Application No. W00 2013 00512, dated Jun. 30, 2016, 4 pages.
Indonesian Examination Report for Indonesian Application No. W00 201104583, dated Jun. 27, 2016, 4 pages.
Mexican Office Action for Mexican Application No. MX/a/2013/001535, dated Jul. 13, 2016 with translation, 4 pages.
Tian, J., et al., "Chitosan microspheres as candidate plasmid vaccine carrier for oral immunisation of Japanese flounder (Paralichthys olivaceus)," Dec. 15, 2008, pp. 220-229, vol. 126, Nos. 3-4, Veterinary Immunology and Immunopathology.
Kumar, S.R., et al., "Potential use of chitosan nanoparticles for oral delivery of DNA vaccine in Asian sea bass (Lates calcarifer) to protect from Vibrio (Listonella) anguillarum," Jul. 2008, pp. 47-56, vol. 25, Nos. 1-2, Fish & Shell Immunology.
Canadian Office Action dated Sep. 9, 2016 for Canadian Application No. 2756883, 4 pages.

* cited by examiner

DRY STORAGE STABILIZING COMPOSITION FOR BIOLOGICAL MATERIALS

CROSS REFERENCE TO RELATED APPLICATION

This application claims priority to U.S. Provisional Application No.: 61/373,711 filed in the United States Patent and Trademark Office on Aug. 13, 2010, the content of which is hereby incorporated by reference herein for all purposes

BACKGROUND OF THE INVENTION

Field of the Invention

The present invention is in the field of stabilizing biological materials in a glassy dry structure.

Related Art

The preservation of the structure and function of biological materials during long-term storage at high temperature and humidity is of fundamental importance to the food, nutraceutical and pharmaceutical industries. Sensitive biological materials, such as proteins, enzymes, cells, bacteria and viruses must often be preserved for long-term storage for later use. Simple freezing is often done when drying is either harmful or unsuitable in the final product. For preservation in a dry state—freeze-drying has traditionally been the most common method. Other methods, such as ambient air-drying, drying under vacuum at ambient temperatures (vacuum-drying), or drying by contacting a fine mist of droplets with warm air (spray-drying) and drying by desiccation are generally not suitable for sensitive bioactives, such as live or attenuated bacteria and viruses. The high drying temperatures used in these methods result in significant damage to the bioactive itself.

Often the freeze drying process may result in a significant loss of activity and damage to the bioactive agent due to the formation of ice crystal during the slow drying process. Freeze-drying combines the stresses due to both freezing and drying. The freezing step of this process can have undesirable effects, such as the denaturation of proteins and enzymes, and rupture of cells. Damage caused by freezing may be circumvented, to a certain degree, by the addition of cryoprotective compounds or agents to the solution. Such protective agents are generally highly soluble chemicals that are added to a formulation to protect cell membranes and proteins during freezing and to enhance stability during storage. Common stabilizers include sugars such as sucrose, trehalose, glycerol, or sorbitol, at high concentrations (Morgan et al., 2006; Capela et al., 2006). Disaccharides, such as sucrose and trehalose, are natural cryoprotectants with good protective properties. Trehalose is a particularly attractive cryoprotectant because it has actually been isolated from plants and live organisms that remain in a state of suspended animation during periods of drought. Trehalose has been shown to be an effective protectant for a variety of biological materials, (see Crowe, J. H., 1983). Several patents disclose the use of trehalose or trehalose in combination with other cryoprotectants for protecting proteins and other biological macromolecules, such as enzymes, serum, serum complement, antibodies, antigens, fluorescent proteins and vaccine components during freezing, drying and rehydration (U.S. Pat. No. 5,556,771).

However, there are some drawbacks associated with the use of trehalose or other disaccharides or monosaccharides as the sole cryoprotectant. Trehalose may not penetrate adequately into the cell to protect active components within the intracellular volume, which may lead to instability upon storage of the freeze-dried substances. In addition, concentrations of trehalose greater than 60% by weight of a given preservation medium are sometimes necessary. An even more serious problem associated with the use of trehalose is that biological materials preserved using trehalose alone are not storage stable for extended periods of time, especially those stored at high temperatures and/or humid environments. Therefore, a significant challenge remains to develop an optimal formulation and drying process that minimizes drying losses while achieving adequate storage stability of the dried material.

Some of the issues associated with the trehalose and the freeze-drying process have been resolved by using a combination of certain formulations and vacuum drying in a glassy state, particularly sugar glasses (U.S. Pat. No. 6,190,701). In those formulations, the bioactive agent is protected within a glassy matrix against hostile environments such as high temperatures and humidity. However, in these formulations, the presence of water as moisture in the environment acts as a plasticizing agent and has the effect of lowering the glass transition temperature (Tg) of the glassy matrix. At higher water contents, the Tg is significantly lowered to the extent that the dry formulation is in the undesirable rubbery or plastic state at room temperature.

The advantages of retaining the glass form of the formulation include increased physical stability of the solid and reduction of deleterious intermolecular reactions. A detailed discussion of the physical chemistry of water-food polymer interactions as relating to the glassy state and their transition temperatures can be found in M. Le Meste, et al. 2002. However, limitations of amorphous systems such as physical instability and higher chemical reactivity, act as a hurdle in their extensive commercialization.

Thus, a need exists for a stabilizing composition that is useful for wide range biological materials. A further need exists for a stabilizing composition that can be effectively used in both freeze-drying processes and drying processes involving ambient-temperature drying. There is also a need for a composition mixture that is less costly than those presently being used. Finally, and importantly, there is a need for a composition mixture that provides stable media for preservation of biological materials over extended periods of time at elevated temperatures and varying degrees of humidity which can be encountered during shipping and storage of materials, while still retaining a significant amount of activity upon rehydration.

All of these needs are met by the composition mixture, drying methods and resulting preserved biological material compositions of the present invention.

SUMMARY OF THE INVENTION

The present invention includes compositions and drying methods for preserving sensitive bioactive materials, such as peptides, proteins, hormones, nucleic acids, antibodies, drugs vaccines, yeast, bacteria (probiotic or otherwise), viruses and/or cell suspensions, in storage.

The composition of the invention includes a carbohydrates mixture of di-, oligo- and polysaccharides and ions of organic acid preferably citric acid and or ascorbic acid. The formulation is prepared by dispersing all the solid components in a solution. The solution is snap-frozen by means known in the art like liquid nitrogen or dry ice to form small beads, strings or droplets. The frozen beads can be stored in a deep-freezer (between −30° C. and −80° C.) for later use in frozen state or placed on trays in a frozen state for drying in a conventional freeze drier. The preferred drying method is optionally initiated by a short purging and structure stabilizing step of the frozen particles under a vacuum pressure of less than <2000 mTORR followed by a primary drying step under vacuum pressure of more than >2000 mTORR and at a desired temperature. During the secondary and final drying step of the material a full vacuum pressure and elevated temperature are applied, to achieve a final desirable water activity of the dry material.

In one particular embodiment, the biological material comprises live bacteria (e.g., probiotic bacteria). Examples of suitable microorganisms include, but are not limited to, yeasts such as *Saccharomyces, Debaromyces, Candida, Pichia* and *Torulopsis*, moulds such as *Aspergillus, Rhizopus, Mucor, Penicillium* and *Torulopsis* and bacteria such as the genera *Bifidobacterium, Clostridium, Fusobacterium, Melissococcus, Propionibacterium, Streptococcus, Enterococcus, Lactococcus, Kocuriaw, Staphylococcus, Peptostrepococcus, Bacillus, Pediococcus, Micrococcus, Leuconostoc, Weissella, Aerococcus, Oenococcus* and *Lactobacillus*. Specific examples of suitable probiotic microorganisms would be represented by the following species and include all culture biotypes within those species: *Aspergillus niger, A. oryzae, Bacillus coagulans, B. lentus, B. licheniformis, B. mesentericus, B. pumilus, B. subtilis, B. natto, Bacteroides amylophilus, Bac. capillosus, Bac. ruminocola, Bac. suis, Bifidobacterium adolescentis, B. animalis, B. breve, B. bifidum, B. infantis, B. lactis, B. longum, B. pseudolongum, B. thermophilum, Candida pintolepesii, Clostridium butyricum, Enterococcus cremoris, E. diacetylactis, E faecium, E. intermedius, E. lactis, E. muntdi, E. thermophilus, Escherichia coli, Kluyveromyces fragilis, Lactobacillus acidophilus, L. alimentarius, L. amylovorus, L. crispatus, L. brevis, L. case* 4 *L. curvatus, L. cellobiosus, L. delbrueckii ss. bulgaricus, L farciminis, L. fermentum, L. gasseri, L. helveticus, L. lactis, L. plantarum, L. johnsonii, L. reuteri, L. rhamnosus, L. sakei, L. salivarius, Leuconostoc mesenteroides, P. cereviseae (damnosus), Pediococcus acidilactici, P. pentosaceus, Propionibacterium freudenreichii, Prop. shermanii, Saccharomyces cereviseae, Staphylococcus carnosus, Staph. xylosus, Streptococcus infantarius, Strep. salivarius ss. thermophilus, Strep. Thermophilus* and *Strep. lactis*.

In one embodiment, the formulation comprises a carbohydrate mixture of di-, oligo-and poly-saccharides, in which the bioactive material is embedded. Examples of a suitable polysaccharide, include but is not limited to, cellulose acetate phthalate (CAP), carboxy-methyl-cellulose, pectin, sodium alginate, salts of alginic acid, hydroxyl propyl methyl cellulose (HPMC), methyl cellulose, carrageenan, gellan gum, guar gum, gum acacia, xanthan gum, locust bean gum, chitosan and chitosan derivatives, collagen, polyglycolic acid, starches and modified starches. Examples of a suitable oligosaccharide, include but is not limited to, cyclodextrins, inulin, FOS, maltodextrins, dextrans, etc.; and combinations thereof. Examples of a suitable disaccharide, include but are not limited to, lactose, trehalose, sucrose, etc. In one particular embodiment, the preferred polysaccharide is sodium alginate or gellan gum. Preferably, the carbohydrate mixture comprises, in percent by weight of total dry matter, 0.1-10% polysaccharides, 1-10% oligosaccharides and 10-90% disaccharides. In an additional embodiment, the carbohydrates mixture comprises di-, oligo- and poly-saccharides in a weight ratio of 10:0.1-4: 0.1-2, and more preferably, wherein the weight ratio of disaccharides/oligosaccharides/polysaccharides is from about 10:0.2:0.1 to about 10:2:1.

In yet another embodiment of the present invention, the polysaccharides in the carbohydrates mixture are cross-linked with divalent metals ions to form a firm hydrogel.

In another embodiment, the composition comprises significant amounts of glass enhancing compounds including salts of organic acids such as lactic acid, ascorbic acid, maleic acid, oxalic acid, malonic acid, malic acid, succinic acid, citric acid, gluconic acid, glutamic acid, and the like. Salts may include cations such as sodium, potassium, calcium, magnesium, and the like. Examples include sodium citrate, sodium lactate, sodium maleate, magnesium gluconate, sodium ascorbate, and the like. Salts having high glass transition temperature (Tg) and high solubility are preferred. The most preferred organic acid is citric acid and its salts (e.g., sodium or potassium citrate, trisodium citrate dehydrate) and ascorbic acid and its salts (e.g., sodium ascorbate, potassium ascorbate, magnesium ascorbate). The preferred total amount of citrate or ascorbate ions in the dry composition is such that the molar ratio of ions to moles of carbohydrates compounds is from about 0.01 to about 0.3 and most preferably from about 0.1 to about 0.2.

Other useful glass enhancers include proteins, protein hydrolysates, polypeptides and amino acids. These include gelatine, albumin, whey protein, soy protein, casein, caseinate, immunoglobulins, soy protein, pea protein, cottonseed protein or other food and dairy or vegetable proteins and/or their hydrolysates. Examples of polyamino acids include polyalanine, polyarginine, polyglycine, polyglutamic acid and the like. Useful amino acids include lysine, glycine, alanine, arginine or histidine, as well as hydrophobic amino acids (tryptophan, tyrosine, leucine, phenylalanine, etc) and a methylamine such as betaine. The preferred total amount of proteins, protein hydrolysates and amino acids in the dry composition is from about 1% to about 30% of the total mass of carbohydrates mixture and most preferable from about 5% to about 20% of the carbohydrates mass. Ideally, compounds that are Generally Recognized As Safe (GRAS) compounds are preferred over those that are not GRAS.

It should be noted that the proper amount of the glass enhancers in the composition may depends on the desired characteristics of the dry composition. The determination of the proper amount of glass enhancers should be made according to the desired storage conditions. For example, a composition containing carbohydrate mixture and protein or protein hydrolysates can be used to enhance the chemical stability of a biological material while being stored under mild temperature and relative humidity, such as 25° C. and 25% RH. Citrate ions may be preferred to comprise the glass enhancer to obtain added benefit of stabilizing at higher temperature and humidity exposure. Alternatively, it can be the case that a combination of citrate and/or ascorbate ions with another glass enhancer, such as protein or protein hydrolysate, is more preferred to comprise the composition.

The preferred mixing process of the biological material and the composition is by adding the total dry composition mixture in a concentrate culture or media solution containing biological material. The weight mass of the biological material in the culture media is typically between about 5% and 30% w/v, and more preferably between about 10% and 20% w/v. the added weight mass of the composition mixture in the culture media is typically between about 10% and about 60%, and more preferably between about 20% and 40%. The final solid content in the mixed slurry is from about 20% to about 60% and more specifically from about 30% to about 50%. Preferably, the solution is mixed at room temperature or slightly warmed to assist in solublizing the materials in the viscous solution (e.g., from 20° C. to 40°

C.). In a variation of the present invention, the total amount of the carbohydrates mixture in the formulation is adjusted to achieve a desired formulation viscosity and density that allowed an efficient drying while avoiding rubbery formation or excessive foaming that may occurs during the drying step. A preferred slurry viscosity is from about 1,000 cP to about 500,000 cP, and most preferred range is from about 10,000 cP to about 300,000 cP. A desired viscosity and density of the final slurry can be achieved by any means known in the art, for example, slightly adjusting the amount of the polysaccharides in the carbohydrates mixture or by degassing or injecting gas such as air, nitrogen, carbon dioxide, argon etc.

The biological material slurry of the present invention is typically snap-frozen to between −30° C. to −180° C., more preferably, the formulation is snap-frozen in liquid nitrogen by atomizing, dripping or injecting into liquid nitrogen bath. Collecting the particles, beads, strings or droplets from the liquid nitrogen bath and drying in a freeze drier or vacuum drier, or alternatively storing them in a deep freezer (between −30° C. and −80° C.) for later use in a frozen form or until drying.

In general, the drying process techniques that are useful include spray drying; lyophilization followed by milling to micronize the powder; atomization onto a cold surface, followed by sublimation and collection of the micronized powder; evaporative drying of a non-frozen solution in a vacuum oven or centrifugal evaporator at temperatures above the freezing temperature of the slurry (−20 to 50° C.), followed by milling to desirable particle size. The resultant powder particles are glassy or crystalline internally with a majority of the glassy materials coating on the surface. The advantage of coating the biological material with glassy materials is to increase physical stability of the product and reduction of deleterious intermolecular reactions within the particle. In a preferred embodiment, the frozen particles is loaded on trays and immediately transferred to a vacuum drying chamber where the drying process proceeds in three major steps including: (1) An optional, short purging and structure stabilizing step of the frozen particles under a vacuum pressure of less than <2000 mTORR, (2) Primary drying step under vacuum pressure of more than >2000 mTORR and at a temperature above the freezing point of the slurry, and (3) Secondary and final drying step of the glassy amorphous material under full vacuum pressure and elevated temperature for a time sufficient to reduce the water activity of the dried formulation to 0.3 Aw or less.

The dried and stable biological composition can be used directly as a flake, or ground into a powder and sieved to an average particle size from about 10 μm to about 1000 μm. The formulation can be administrated directly to an animal, including man, as a concentrated powder, as a reconstituted liquid, (e.g., beverage), or it can be incorporated either in flake or powder form into an existing food or feed product.

These and other advantages and features of the present invention will be described more fully in a detailed description of the preferred embodiments which follows.

DETAILED DESCRIPTION OF THE INVENTION

Definitions

Figure 1:
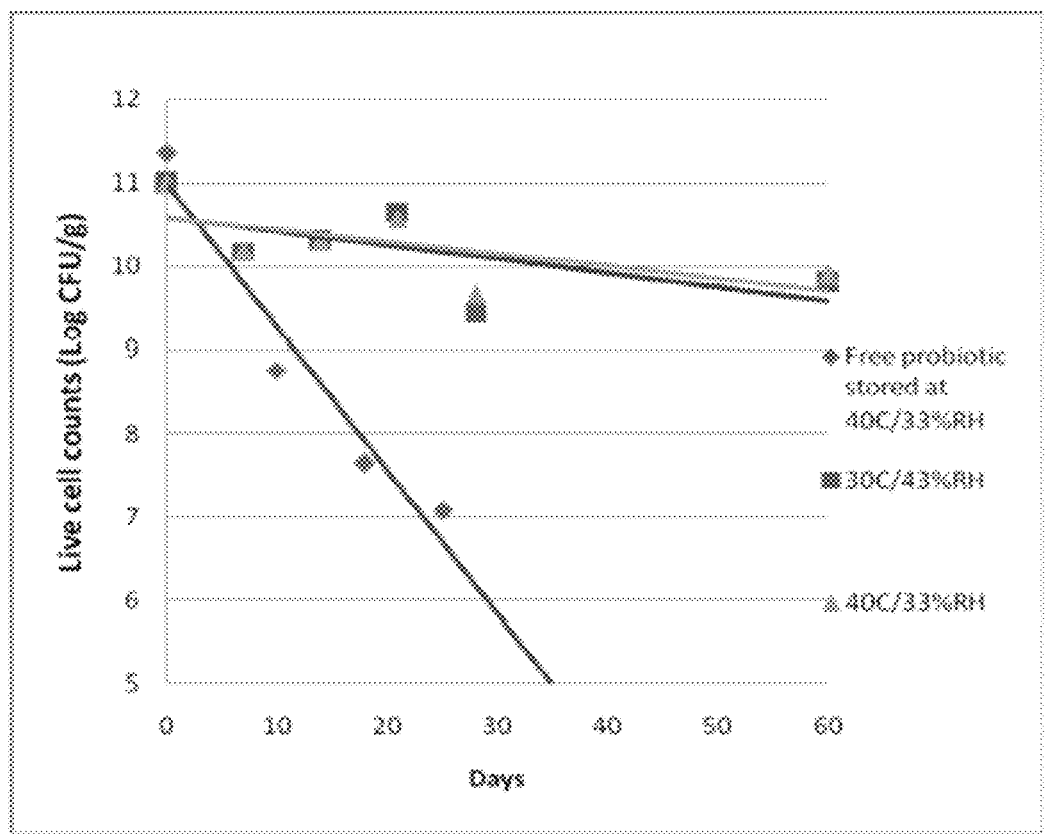
FIG. 1 shows acceleration stability of commercially available probiotic bacteria and probiotic bacteria in dry composition of the present invention.

It is to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a protein" includes singular protein or a combination of two or more proteins; reference to "enzyme", "bacteria", etc., includes singular or mixtures of several types, and the like.

In describing and claiming the present invention, the following terminology will be used in accordance with the definitions set out below.

"Biological material", "biological composition", or "bioactive formulation" refers to preparations, which are in such a form as to permit the biological activity of the bioactive ingredients or agents to be unequivocally effective.

"Glass enhancer" is a chemical compound with the ability to form amorphous or glassy structure below a critical temperature, the glass transition temperature (Tg). If a glass enhancer is dried below its Tg, glass will form. However, if the glass enhancer is dried above its Tg, then glass does not form. During the formation of glassy structure, biological substance can become embedded within the glass structure. Glass enhancers suitable for use with the present invention include, but are not limited to, include salts of organic acids such as lactic acid, ascorbic acid, maleic acid, oxalic acid, malonic acid, malic acid, succinic acid, citric acid, gluconic acid, glutamic acid, and the like. Salts may include cations such as sodium, potassium, calcium, magnesium, phosphate and the like. Other useful glass enhancers include proteins, protein hydrolysates, polypeptides and amino acids. A combination of glass forming agents is also contemplated within a single composition. The process used to obtain a glassy structure for the purposes of this invention is generally a solvent sublimation and/or evaporation technique. Ideally, compounds that are GRAS compounds are preferred over those that are not GRAS.

"Carbohydrates" or "polyhydroxy compound" refers to saccharides predominantly composed of carbon, hydrogen, and oxygen. A saccharide typically composed of a sugar backbone of repeating structural units linked in linear or non linear fashion, some of which contain positively or negatively charged chemical groups. The repeating units may range from two to several million. Useful saccharides include reducing and non reducing sugars and sugar alcohols, disaccharides, oligosaccharides, water soluble polysaccharides and derivatives thereof. Two monosaccharides linked together form a disaccharide. The two monosaccharides used to form a disaccharide can be the same or different. Examples of disaccharides which can be used in the carbohydrates mixture of the present invention include, sucrose, trehalose, lactose, maltose, isomaltose. Sulfated disaccharides may also be used. Small number of monosaccharides linked together (typically from three to ten) form an oligosaccharide. The monosaccharides used to form an oligosaccharide can be the same or different components sugars. Examples of oligosaccharides suitable for use include, inulin, maltodextrins, dextrans, fructo-oligosaccharides (FOS), galacto-oligosaccharides (GOS), mannan-oligosaccharides (MOS) and combinations thereof. Large number of monosaccharides linked together (typically more than ten) form a polysaccharide. The monosaccharides used to form a polysaccharide can be the same or different components sugars. Examples of polysaccharides suitable for use include, but are not limited to, methylcellulose, hydroxypropylcellulose, hydroxyethylcellulose, and hypromellose; soluble starches or starch fractions, xanthan gum, guar gum, pectins, carrageen, galactomannan, gellan gum, including any derivatives of these, cellulose acetate phthalate (CAP), carboxy-methyl-cellulose, sodium alginate, salts of alginic acid, hydroxyl propyl methyl cellulose (HPMC), gum acacia, locust bean gum, chitosan and chitosan derivatives, collagen, polyglycolic acid, starches and modified starches and cyclodextrins.

A "stable" formulation or composition is one in which the biologically active material therein essentially retains its physical stability, chemical stability, and/or biological activity upon storage. Stability can be measured at a selected temperature and humidity conditions for a selected time period. Trend analysis can be used to estimate an expected shelf life before a material has actually been in storage for that time period. For live bacteria, for example, stability is defined as the time it takes to lose 1 log of CFU/g dry formulation under predefined conditions of temperature, humidity and time period.

"Viability" with regard to bacteria, refers to the ability to form a colony (CFU or Colony Forming Unit) on a nutrient media appropriate for the growth of the bacteria. Viability, with regard to viruses, refers to the ability to infect and reproduce in a suitable host cell, resulting in the formation of a plaque on a lawn of host cells.

"Ambient" room temperatures or conditions are those at any given time in a given environment. Typically, ambient room temperature is 22-25° C., ambient atmospheric pressure, and ambient humidity are readily measured and will vary depending on the time of year, weather and climactic conditions, altitude, etc.

"Water activity" or "Aw" in the context of dried formulation compositions, refers to the availability of water and represents the energy status of the water in a system. It is defined as the vapor pressure of water above a sample divided by that of pure water at the same temperature. Pure distilled water has a water activity of exactly one or Aw=1.0.

"Relative Humidity" or "RH" in the context of storage stability refers to the amount of water vapor in the air at a given temperature. Relative humidity is usually less than that required to saturate the air and expressed in percent of saturation humidity.

"Dry" and variations thereof refer to a physical state that is dehydrated or anhydrous, i.e., substantially lacking liquid. Drying includes for example, spray drying, fluidized bed drying, lyophilization, and vacuum drying.

"Lyophilize" or freeze drying refers to the preparation of a composition in dry form by rapid freezing and dehydration in the frozen state (sometimes referred to as sublimation). Lyophilization takes place at a temperature which results in the crystallization of the polymers. This process may take place under vacuum at a pressure sufficient to maintain frozen product, preferably lower than about <2000 mTORR.

"Primary drying" or "Liquid drying", with regard to processes described herein, refers to the dehydration drying that takes place from the time of thawing the frozen particles to the point where secondary drying starts. Typically, the bulk of primary drying takes place by extensive evaporation, while the product temperature remained significantly lower than the temperatures of the heat source. This process may take place under vacuum at a pressure sufficient to maintain thawed product, preferably greater than about >2000 mTORR.

"Secondary drying", with regard to processes described herein, refers to a drying step that takes place at temperatures above freezing temperatures of the formulation and near the temperature of the heat source. This process may take place under vacuum at a pressure sufficient to reduce the water activity of a formulation, preferably less than about <1000 mTORR. In a typical formulation drying process, a secondary drying step reduces the water activity of the formulation to an Aw of 0.3 or less.

The compositions and drying methods of the present invention solve the problem of providing a cost effective and industrially scalable frozen or dry formulations containing sensitive bioactive materials, such as peptides, proteins, hormones, nucleic acids, antibodies, drugs, vaccines, yeast, bacteria, viruses and/or cell suspensions, with a significantly extended lifetime in the dry state. The invention provides a preservation composition and a drying method comprising a biological material surrounded by amorphous glassy structure of highly soluble compounds. The freezing and drying process comprises: mixing the biological material and the composition in a liquid slurry, snap-freezing said composition slurry in liquid nitrogen to form droplets, strings or beads, purging the frozen particles under high vacuum followed by drying the bioactive material in a sugar glass formation by evaporating the moisture under a regimen of reduced pressure while supplying heat to the composition.

The present invention is based on the remarkable discovery that biological materials can be protected in glassy structure while retaining substantial activity. When the biological material is combined with the composition mixture and vacuum dried according to the present invention a superior stability was achieved during extended time exposure to harsh temperature and humidity conditions. The present invention includes compositions containing a biological material, a mixture of soluble carbohydrates and glass enhancing carboxylic acid salts. The compositions of the invention are inherently different in their physical structure and function from non-viscous or concentrated sugary compositions that were simply dried under a typical drying process. For example, U.S. Pat. No. 6,919,172 discloses an aerosolized powder composition for pulmonary administration, which contains a mixture of various carbohydrates and sodium citrate. However, the composition described in the patent lacks the additional proteinous compound that is essential for added stability and for the formation of a desirable physical structure during drying of solutions having high concentration of sugars. The described composition in this patent also lacks viscosity or hydrogel structure, which allows an efficient drying of thawed or unfrozen solution for enhanced glass formation. In contrast, the composition and drying process of the present invention overcomes all these issues while achieving a superior stability of the biological material.

Enhanced glassy structure was usually achieved in the prior art by foaming or boiling the solution under vacuum to facilitate effective drying. The foaming step generally resulted in an extensive boiling and eruption of the solution that is an unavoidable consequence of the drying of unfrozen solution, and as a result, only a very low loading capacity of solution in a vial or a vessel can be achieved (see for example U.S. Pat. No. 6,534,087, in which the thickness of the final foamed product is less than 2 mm). The compositions and drying methods of the present invention avoid boiling and foaming of the formulation thereby enabling much higher loading of material per drying area and, as a result, can be easily scaled up to the production of large quantities of material without the use of specifically designed vessels and trays or equipment.

A wide range of biological materials can be used with the inventive composition to form the aqueous preservation medium of the present invention. This preservation medium can then be subjected to the drying processes of the present invention to make a stable dry powder of biological material. These biological materials, include, without limitation: enzymes, such as pancreatic enzymes, lipases, amylases, protease, phitase, lactate dehydrogenase; proteins, such as insulin; vaccines; viruses, such as adenovirus; cells, including prokaryotic cells (including bacteria) and eukaroytic cells, other biological materials, including drugs, nucleic acids, and lipid vesicles.

Probiotic bacteria have been shown to benefit particularly from the compositions and drying methods of the present invention. The stable dry probiotic powder is prepared according to the compositions and methods of the invention including mixing fresh, frozen or dry cultures of probiotic bacteria with a mixture of carbohydrates and glass enhancing compounds, snap-freezing the viscous formulation in liquid nitrogen to form frozen solid droplets, strings or beads, and vacuum drying by initially applying sufficient vacuum pressure to purge and stabilize the structure of the frozen particles, increase the formulation temperature above the freezing temperature and supplying a heat source of 20° C. and higher to facilitate primary water removal. Maintaining the temperature of the formulation above the freezing point can be accomplished by adjusting the vacuum pressure and by conduction of heat to the formulation. To complete the drying process and further reduce the water activity of the formulation below Aw of 0.3 or lower, a secondary drying step is applied at maximum vacuum pressure and at elevated temperature up to 70° C. Such a composition can remain stable in harsh storage conditions such as 40° C. and 33% RH for 60 days or more.

Preparation of the Compositions

The composition for the preparation of stable frozen or dry powder of biological materials according to the invention, include a carbohydrate mixture and glass enhancer. Such materials, when mixed with the preferred bioactive material form beads strings or droplets in liquid nitrogen and can be efficiently dried in an amorphous glassy structure according to methods of the invention and to provide large quantities of stable dry compositions for storage and administration of said bioactive material (see FIG. 1—for physical observations and water activity (Aw) of different formulation after drying). The carbohydrates mixture provides structural stability to the formulation and/or physical and chemical protective benefits to the bioactive materials and prevents or reduces the adverse effects upon reconstitution or rehydration.

The polysaccharide fraction in the carbohydrate mixture can provide thickening viscosity to the formulation and better control over the formulation density properties under vacuum pressure and increased structural strength to the dried formulation compositions of the invention. The preferred polysaccharides, particularly for live organisms, are water soluble gums, because of their distinctive characteristic to form viscous gel at mild temperatures. Gums at certain concentration were also found to effectively stabilize the formulation structure under vacuum, by providing appropriate viscosity and density to the formulation and allowing an effective drying of the formulation during the primary liquid drying step at a particular viscosity. Certain gums can also form hydrogel by cross-linking with divalent or multivalent cations (e.g., alginates, pectins, chitosan) or by temperature or pH changes (e.g., gelatins, CMC, CAP, gellan gum). Hydrogeled solutions would prevent problems associated with vacuum drying of unfrozen solutions.

The disaccharide fraction in the carbohydrate mixture includes various sugars and sugar alcohols. The preferred disaccharide is one that does not crystallize and/or damage or destabilize the biologically active material in the formulation at freezing temperatures (e.g., lower than −20° C.) and during water removal. For example, bioactive material can be physically embedded in glass forming sugars such as sucrose, lactose or trehalose to promote retention of molecular structure throughout the drying process and impart structural rigidity to the amorphous matrix in the dry state. A suitable disaccharide would effectively replace water of hydration lost during drying, to prevent damage to cell membranes and denaturation of enzymes (see review by Crowe et al., 1998). Other functions of the disaccharide in the composition can include protecting the bioactive material from exposure to damaging light, oxygen, oxidative agents and moisture. A suitable disaccharide must readily dissolve in a solution. Trehalose is a particularly attractive protectant because it is a non-reducing disaccharide found in plants and living organisms (e.g., bacteria, fungi and invertebrates such as insects and nematodes) that remain in a state of dormancy during periods of drought. Trehalose has been shown to be an effective protectant for a variety of biological materials including proteins and other biological macromolecules, such as enzymes, serum, antibodies, antigens and vaccine components (Sanchez et al., 1999, Intl. J. Pharm. 185, 255-266; Esquisabel et al., 1997, J. Microencapsulation, 14, 627-638). In some cases, it can be beneficial to include two or more different disaccharides such as a mixture of trehalose and sucrose to inhibit the formation of crystals, to enhance the stability of the dried bioactive material formulation in storage conditions for extended time periods and to reduce costs.

The oligosaccharide fraction in the carbohydrate mixture includes inulin, maltodextrins, dextrans, fructo-oligosaccharides (FOS), galacto-oligosaccharides (GOS), mannan-oligosaccharides (MOS) and combinations thereof. The oligosaccharides mitigate several problems associated with the use of trehalose alone as a protectant for a variety of preserved biological materials. Although very effective in protecting the biological material during dehydration and rehydration, trehalose alone as a stabilizer does not provide desirable storage stability for extended periods of time, especially at high temperatures and/or humid environments.

This problem was resolved in the present invention with the addition of oligosaccharides, preferably inulin, to the carbohydrate mixture.

The preferred mass ratio of the saccharides in the carbohydrates mixture is 10:0.1-4:0.1-2 disaccharides/oligosaccharides/polysaccharides and more preferably, wherein the weight ratio of disaccharides/oligosaccharides/polysaccharides is from about 10:0.2:0.1 to about 10:2:1. Preferably, the carbohydrate mixture comprises, in percent by weight of total dry matter, 10-90% disaccharides, 1-10% oligosaccharides and 0.1-10% polysaccharides.

The glass structure enhancers of the present invention include the salts of organic acids such as lactic acid, ascorbic acid, maleic acid, oxalic acid, malonic acid, malic acid, succinic acid, citric acid, gluconic acid, glutamic acid, and the like. Salts may include cations such as sodium, potassium, calcium, magnesium, buffer salts, phosphate buffer and the like. Examples include sodium citrate, sodium lactate, sodium maleate, magnesium gluconate, sodium ascorbate, potassium ascorbate, phosphate buffered salts and the like. Generally, multivalent anions form glasses more readily with a higher Tg than monovalent anions. The preferred anion will have a high Tg and sufficient solubility to inhibit crystallization and thereby form a robust glassy structure. In some cases, mixtures of organic salts may be useful (e.g. sodium citrate and sodium ascorbate). Sodium citrate was found to interact with the hydroxyl groups of the sugar molecule and form bonding via its carboxyl groups, which results in a dramatic increase in the glass transition temperature of vitrified sucrose (Kets et al., 2004. Citrate increases glass transition temperature of vitrified sucrose preparations Cryobiology, 48:46-54). Sodium citrate is a common food additive affirmed as GRAS (21 CFR 184.1751—Sodium citrate). Additional functions of the sodium citrate in the compositions are associated with its buffering capacity and preventing drastic changes in pH of the liquid medium during freezing, which can lead to the denaturation of the protein being freeze-dried.

Other suitable glass enhancers that are included in the composition to further increase its stability include proteins, protein hydrolysates, polypeptides and amino acids. Preferably, casein or pea and more preferably, hydrolyzed casein or hydrolyzed pea proteins, are used. "Hydrolyzed protein" refers to protein that has been subjected to partial or full acid or enzymatic hydrolysis to yield a hydrolyzed protein having a molecular weight of from about 1 kDa to about 50 kDa. Preferably, at least 20% of the protein substrate is converted into peptides having molecular masses from 200 to 2000 dalton. The hydrolyzed protein has approximately the same amino acid composition as full protein and may be obtained from any number of commercial sources. Being hypoallergenic, hydrolyzed protein may advantagously be used in certain food for hyper sensitive consumers such as infants and elderly.

The amount of glass enhancers used in the composition will vary depending on the overall composition and its intended drying storage conditions. Generally, the molar ratio of the glass enhancers to the total carbohydrates will be from about 0.01 to about 0.3. A preferred composition comprises a molar ratio of about 0.1-0.2.

A preferred composition comprises from about 0.5% to about 90% of a carbohydrate component including at least a di-, oligo- and poly-saccharide and a protein component comprising about 0.5% to about 40% of a hydrolyzed protein. More preferably, the composition comprises about 30% to about 70% of carbohydrate component and about 10% to about 40% of a glass enhancer component such as a protein hydrolyzed protein and carboxylic acid, wherein the carbohydrate component comprises about 10% to 90% and more preferably from about 40% to 80% of a disaccharide; about 1% to about 10% and more preferably from about 5% to 10% of an oligosaccharide; and about 0.1 to about 10% and more preferably from about 5% to about 10% of a polysaccharide. The composition further comprises a salt of an organic acid which is considered to be another glass enhancer component and comprises between about 0.5% and 20% carboxylic acid, based on the total weight of the composition.

The solution containing the biological material and the stabilizing composition of the present invention can include a substantial amount of total solids (constituents minus the solvent, such as water), from about 20% to about 60% preferably about 30-50% weight percent. A major portion of the total solids can consist of the bioactive material, the carbohydrate mixture and the glass enhancers. For example, the bioactive material can be present in the formulation in a concentration ranging from about 5% and 30% w/v, preferably about 10-20% w/v. The weight mass of the composition mixture in the culture media is typically between about 10% and about 60%, preferably about 20-40%. The viscosity of formulations of the invention is typically greater than 1000 centipoises (cP); more preferably, greater than 5,000 cP; and most preferably greater than 10,000 cP.

Methods of Preparing Stable Dry Formulations

Various drying techniques can effectively be used to dry the composition. These methods, while less complicated and less costly than freeze-drying or vacuum drying, are generally more destructive to biological materials. Many biological materials are more prone to gross conformational changes and unwanted reactions when preserved using methods that take place at ambient or higher temperature than when freeze-drying or chill drying is used. As a result, even where presently known protective agents are used, the activity of many rehydrated biological materials is both unsatisfactory in its own right, and significantly less than if preserved by low temperature drying.

Preferred methods for preparing stable dry formulations containing bioactive materials include: (1) preparation of a viscous slurry formulation by mixing the bioactive material with the composition of the present invention in an aqueous solution, (2) snap-freezing the slurry formulation to form solid frozen particles, (3) Optionally, subjecting the frozen particle to high vacuum pressure for a short time to purge the particles and stabilize their structure, (4) removing water by evaporating the moisture at a temperature above the formulation freezing temperature, (5) further reducing the formulation water activity to lower than 0.3 Aw under full vacuum and elevated temperature.

For example, a dry form of bioactive material can be formulated into a solution or suspension containing the composition powder mixture. The composition mixture can be dissolved into a warm aqueous solution with low sheer agitation before cooling and mixing with the bioactive material. The bioactive material, such as cultured virus or bacterium, can be concentrated and separated from the culture media by centrifugation or filtration before re-suspension into the formulation. Alternatively, the totality of the water in the formulation is provided in the liquid of the concentrated biological material. The suspension is maintained at a temperature slightly above room temperature and the dry composition powder mixture is slowly added to the warm (25° C. to 40° C.) suspension containing the biological material. The suspension is gently agitated in a planetary mixer until all components are fully dispersed or dissolved and uniform slurry is obtained.

The viscous solution can be then cross-linked to form a hydrogel (depending on the polysaccharide properties) by adding metal ions or changing the temperature or pH of the slurry and then dried according to the drying methods of the invention. Alternatively, the slurry can be snap-frozen by atomizing through a nozzle, dripping or injecting in dry ice or liquid nitrogen bath to form small particles or solid droplets strings or beads. The frozen solid particles can be stored in a deep freezer between −30° C. and −80° C. for later use as a stable frozen product or until drying. The preferred drying method is vacuum drying where the product temperature is maintained slightly above its freezing temperature. The frozen droplets or beads are placed on trays at a loading capacity from about 0.1 kg/sq ft to about 1.5 kg/sq ft and dried according to the method of the invention. Preferably, the drying process is initiated by a short purging step, which allows the product acclimation to initial temperature and structure of the frozen particles to relax and stabilize and excess air degassed. Typically, the purging step takes between 1 and 60 minutes depending on the product viscosity and tray loading. The beads or particles should remain in a solid frozen form during the entire purging step. The product temperature is then brought to above its freezing temperature and primary drying step followed until all free water is evaporated from the product. Once the formulation temperature reached the desired temperature, heat is adjusted to maintain that temperature and the primary liquid drying step by evaporation is progressed. At this step the formulation is already thawed and accelerated water evaporation take place without any boiling or foaming. The drying process is completed with an additional secondary drying phase at maximum vacuum and elevated temperature.

Typical methods in the prior art involve extensive foaming and/or splattering and violent boiling that can be damaging to sensitive biologicals and cause difficulties for industrial scale up at high loading capacity (see for example U.S. Pat. No. 6,534,087, where the applied vacuum pressure result in violent boiling and foaming). However, the current compositions and methods avoid any boiling or foaming of the formulation while achieving a significantly faster drying rate and enabling a high loading capacity of the formulation. Additionally, a complete and efficient degassing of viscous liquid slurries is difficult and may require an extended period of time. These obstacles were all resolved in the present invention by using a suitable composition that allows an effective primary liquid drying that forms a glassy structure without any boiling and excessive foaming. The loading of solid frozen particles on a tray as oppose to slurry or viscous syrup allows much higher loading capacity per drying area on trays than was afforded according to the prior art.

In one preferred example of the present invention, the biological material is live concentrate probiotic bacteria culture. A powder composition mixture preferably contains 1-4% sodium alginate or gellan gum, 50-75% trehalose, 1-10% inulin or FOS, 10-20% protein hydrolysates, such as casein, whey, pea, soy or cottonseed hydrolysates and 1-10% sodium citrate or sodium ascorbate. The probiotic culture can be fresh, frozen or already dried in a form of dry powder. The composition mixture is added to the concentrated probiotic culture media to bring the solid content of the solution mixture to 40-60% (w/w) and the pH adjusted to 6.5-7.5 with phosphate or citrate ions. The solution is mixed at a temperature slightly above the room temperature (typically between 25° C.-37° C.) until all the components are completely dissolved. The viscous slurry is dripped in liquid nitrogen to form small droplets or beads which are then removed from the liquid nitrogen, packed in bags and stored in a deep freezer at −80° C. until drying.

A typical drying method of live probiotic bacteria include; spreading the solid frozen beads on trays in a uniform layer at a loading capacity between 100-1500 g/sq ft and the trays are immediately placed in a freeze drier. Vacuum pressure is then applied at about 1000 mTORR or lower and depending on the freeze drier size and type of heat source, the shelf temperature adjusted to maintain the particles at about −20 to about −30° C. The solid frozen beads are allowed to purge for about 1 to about 60 minutes and vacuum adjusted to between 2000 and 10,000 mTORR and heat transfer increased to raise the formulation temperature to between −10° C. and +0° C. These temperature and vacuum pressure conditions are maintained during the primary liquid drying step which may last from a few hours and up to 24 hours depending on the tray loading. At some point during the primary drying process, the rate of evaporation of solvent slows and the formulation temperature begins to increase due to excess supply of heat in the drying chamber. This point indicates the end of the primary drying step in this invention. As solvent is driven out from the formulation, the glass forming compounds in the solution become concentrated and thicker until it stops flowing as a liquid and form an amorphous and/or stable glassy structure.

A secondary drying step is then followed at maximum vacuum and formulation temperature between 30° C. and 50° C. The purpose of the secondary drying step is to remove the remaining entrapped or bound moisture and provide a composition that is stable in storage for an extended period of time at ambient temperatures. The secondary drying step may last several hours and its ending point is when the formulation is completely dry and its water activity lower than 0.3 Aw.

The drying methods of the invention result in a biologically active material that is encased within an amorphous glassy structure, thereby preventing the unfolding or denaturation of proteins and significantly slowing molecular interactions or cross-reactivity, due to greatly reduced mobility of the compound and other molecules within the amorphous glassy composition. As long as the amorphous solid structure is maintained at a temperature below its glass transition temperature and the residual moisture remains relatively low (i.e., below Aw of 0.5), the probiotic bacteria can remain relatively stable. It should be noted that achieving a glassy structure is not a prerequisite for long term stability as some biological materials may fare better in a more crystalline state.

The dried glassy structure can be used en bloc, cut into desired shapes and sizes, or crushed and milled into a free flowing powder that provides easy downstream processing like wet or dry agglomeration, granulation, tableting, compaction, pelletization or any other kind of delivery process. Processes for crushing, milling, grinding or pulverizing are well known in the art. For example, a hammer mill, an air mill, an impact mill, a jet mill, a pin mill, a Wiley mill, or similar milling device can be used. The preferred particle size is less than about 1000 μm and preferably less than 500 μm.

The compositions and methods described herein stabilize the biological material and preserve its activity for an extended storage period at above ambient temperature and relative humidity. For example, the compositions are tested for stability by subjecting them at elevated temperature (e.g., 40° C.) and high humidity (e.g. 33% RH) and measuring the biological activity of the formulations. As an example for live probiotic bacteria, results of these studies demonstrate that the bacteria formulated in these compositions are stable for at least 60 days. Stability is defined as time for one log CFU/g potency loss. Such formulations are stable even when high concentrations of the biologically active material are used. Thus, these formulations are advantageous in that they may be shipped and stored at temperatures at or above room temperature for long periods of time.

EXAMPLES

The following examples are offered to illustrate, but not to limit the claimed invention.

Example 1

Preparation of Dry and Stable Composition
Basic Carbohydrates Mixture
About 70 g of trehalose (Cargill Minneapolis, Minn.), about 5 g of instant Inulin (Cargill Minneapolis, Minn.) and about 3 g of sodium alginate (ISP Corp., Wayne, N.J.) were uniformly mixed in dry form.
Basic Glass Enhancers Mixture
About 17 g of casein hydrolysate or pea hydrolysate (ultra filtrated hydrolysates, Marcor, Carlstadt, N.J.) and 5 g of sodium citrate or sodium ascorbate (Sigma, St. Louis, Mo.) were uniformly mixed in dry form.
Stabilization of Probiotic Bacteria
Fresh concentrate of *Lactobacillus rhamnosus*. (100 ml at 10% solids, direct from fermentation harvest) was added in a blender and maintained at 35° C. About 78 g of basic carbohydrates mixture and about 22 g of the basic glass enhancer mixture were slowly added to the probiotic culture and mixing was carried out at 35° C. for 10 minutes. The viscous slurry was then transferred to a vessel having a perforated bottom and allowed dripping into a bath containing liquid nitrogen. The beads were then removed from the liquid nitrogen and immediately transferred to drying.
Drying of the Frozen Beads Containing Probiotic Bacteria
The frozen beads were spread on a tray at a loading capacity of 200 g/sq ft and immediately placed on a shelf in a freeze drier (Model 25 SRC, Virtis, Gardiner, N.Y.). Vacuum was then adjusted to between 2000-2700 mTORR and shelf temperature raised to +30° C. These temperature and vacuum pressure settings were maintained for 5 hours. Optionally, the temperature of the frozen beads was acclimatized to about −20° C. before initiating the primary liquid drying by applying a vacuum pressure at about 1000 mTORR and allowing the solid frozen beads to purge for about 10 minutes. The primary drying step was then followed by adjusting the vacuum pressure to between 2000-2700 mTORR and shelf temperature raised to +30° C. These temperature and vacuum pressure settings were maintained for 5 hours. A secondary drying step was then followed at full vacuum (150-200 mTORR) and shelf temperature maintained at between 30° C. and 50° C. for additional 3 hours. The formulation was completely dried and its water activity measured by a Hygropalm Aw1 instrument (Rotonic Instrument Corp., Huntington, N.Y.) at Aw=0.23.

Example 2

Storage Stability of the Dry Probiotic Bacteria
FIG. 1 shows the storage stability under two different accelerated storage conditions of 40° C. and 33% RH and 30° C. and 43% RH of dry stable probiotic bacteria from Example 1 and commercially available dry probiotic bacteria (Culturelle, Amerifit, Inc., Cromwell, Conn.). The commercial probiotic bacteria completely lost its viability within the first few weeks under the accelerated storage conditions, while the dry composition of the probiotic bacteria of the present invention lost only 1.18 logs after 60 days at 30° C. and 43%RH and only 1.09 logs at 40° C. and 33% RH.

Example 3

Scale-Up Production of Stable Dry Composition Containing Probiotic Bacteria *Lactobacillus Rhamnosus*.
*Lactobacillus rhamnosus* (400 g frozen concentrate from a commercial source) was thawed at 37° C. in a jacketed dual planetary mixer (DPM, 1 qt, Ross Engineering, Inc. Savannah, Ga.) and the solid content adjusted to 10% solids wt with distilled water). About 212 g of trehalose (Cargill Minneapolis, Minn.), about 20 g of instant Inulin (Cargill Minneapolis, Minn.), about 12 g of sodium alginate (ISP Corp., Wayne, N.J.), about 136 g of casein hydrolysate (ultra filtrated hydrolysates, Marcor, Carlstadt, N.J.) and about 20 g of sodium ascorbate (Sigma, St. Louis, Mo.) were uniformly mixed in dry form. The powders mixture was slowly added to the probiotic culture and mixing was carried out at 40 RPM and 37° C. for 10 minutes. The slurry was then transferred to a vessel having a perforated bottom and allowed to drip into a bath containing liquid nitrogen. The beads were then removed from the liquid nitrogen, placed in sealed aluminum foiled bag and stored in a deep freezer at −80° C. for several weeks.
For drying, the frozen beads were evenly spread on trays at a loading capacity ranging from 500 up to 1500 g/sq ft and the trays placed on shelves in a freeze drier (Model 25 SRC, Virtis, Gardiner, N.Y.). A primary liquid drying step was started by adjusting the vacuum pressure to between 2000-2700 mTORR and product temperature raised and stabilized between −10 and −5° C. Over time (about 10-16 h) the product temperature increased to about 20 to 25° C. at which point a secondary drying step initiated at maximum vacuum (150-200 mTORR) and product temperature maintained at between 30 to 40° C. for additional 14 hours. The formulation was completely dried and its water activity measured at 0.23 Aw.

Example 4

Scale-Up production of Stable Dry Composition Containing Probiotic Bacteria *Bifidobacterium Lactis*.
*Bifidobacterium lactis* (400 g frozen concentrate from a commercial source) was thawed at 37° C. in a jacketed dual planetary mixer (DPM, 1 qt, Ross Engineering, Inc. Savannah, Ga.). About 212 g of trehalose (Cargill Minneapolis, Minn.), about 20 g of instant Inulin (Cargill Minneapolis, Minn.), about 12 g of sodium alginate (ISP Corp., Wayne, N.J.) and about 20 g of sodium ascorbate (Sigma, St. Louis, Mo.) were uniformly mixed in dry form. The powders mixture was slowly added to the probiotic culture. About 136 g of pea hydrolysate (ultra filtrated hydrolysates, Marcor, Carlstadt, N.J.) was dissolved in 80 g distilled water and the mixture shortly microwaved or warmed in a water bath to 60° C. until complete dissolution and then cooled down to about 35° C. The dry mix powder and the solution containing pea protein hydrolysate were added to the probiotic concentrate and mixing was carried out at 40 RPM and 37° C. for 20 minutes. The slurry was then transferred to a vessel having a perforated bottom and allowed to drip into a bath containing liquid nitrogen. The beads were then removed from the liquid nitrogen, placed in sealed aluminum foiled bag and stored in a deep freezer at −80° C. for several weeks.

For drying, the frozen beads were evenly spread on trays at a loading capacity of 800 g/sq ft and the trays placed on shelves in a freeze drier (Model 25 SRC, Virtis, Gardiner, N.Y.). A primary liquid drying step was started by adjusting the vacuum pressure to between 2000-2700 mTORR and product temperature raised and stabilized between −10 and −5° C. Over time (about 10-16 h) the product temperature increased to about 20 to 25° C. at which point a secondary drying step initiated at maximum vacuum (150-200 mTORR) and product temperature maintained at between 30 to 40° C. for additional 14 hours. The formulation was completely dried and its water activity measured at 0.23 Aw.

Example 5

Preparation of a Hydrogel Formulation Containing Probiotic Bacteria *Bifidobacterium Lactis*:

Concentrated probiotic slurry of *Bifidobacterium lactis* is prepared according to Example 1. To the basic formulation, 0.5 g of dibasic calcium phosphate is added, followed by 0.5 g of gluconolactone. The slurry is allowed to harden at room temperature over the next 2 hours to form a solid hydrogel. The firm gel is sliced to thin and long threads, using a commercially available slicer/shredder. The thin threads are directly loaded on trays in wet form or snap-frozen in liquid nitrogen and loaded on a tray at a loading capacity of 500 g/sq ft and placed in a freeze drier for drying as described in Example 3. The water activity (Aw) of the formulation is 0.05 (Measured by HygroPalm Awl, Rotonic Huntington, N.Y.). The dry formulation is further ground to fine powder using standard hammer milling equipment and sieved through 50-250 micron screens.

Example 6

Figure 2:
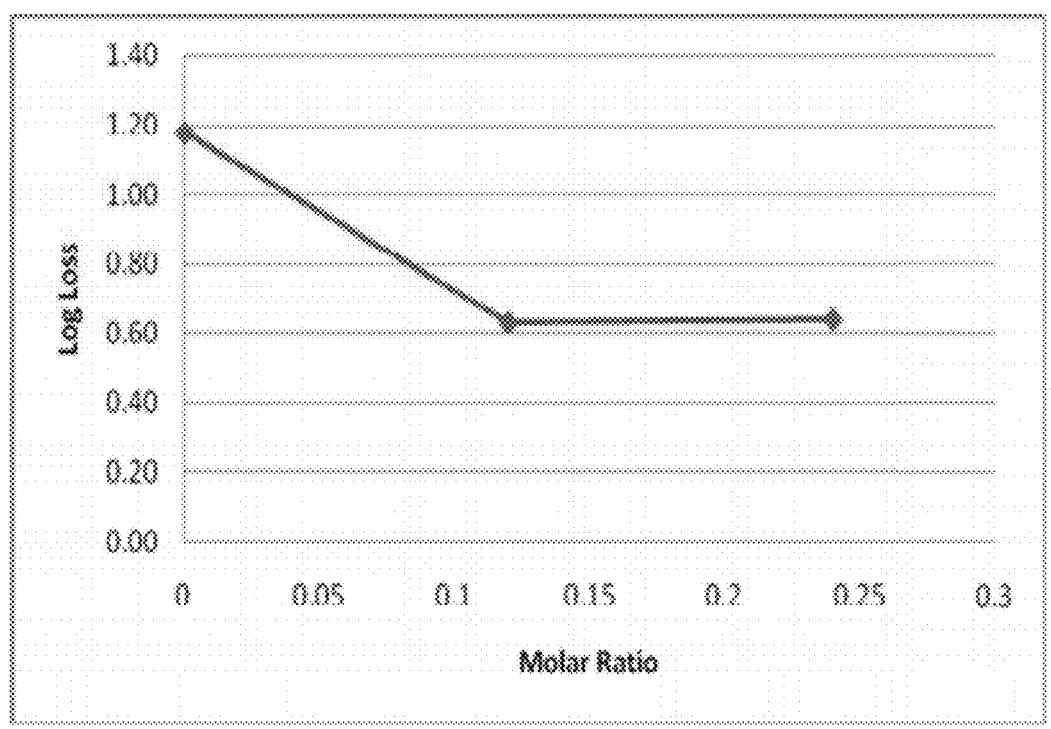
FIG. 2 shows the effect of various molar ratios between the glass enhancers and carbohydrates mixture in the composition on probiotic stability (*L. paracasei*) under accelerated storage conditions (37° C. and 33% RH).

Optimization of the Molar Ratio Between the Glass Enhancers and Carbohydrates Mixture Several compositions containing various molar proportions of glass enhancers and carbohydrates mixture were prepared according to Example 1. A concentrated culture of the probiotic bacteria *L. paracasei* was obtained from a commercial source and prepared in a dry composition as described in Example 1 except that the slurry was immediately loaded on trays in wet form without snap-freezing and purging steps. The slurry was dried in primary and secondary stages as described in Examples 1 and 3 except that the shelf temperature was raised to 40° C. during primary and secondary drying stages. The stable powder was subjected to acceleration storage conditions at 37° C. and 33% RH for 84 days. FIG. 2 show the effect of various molar ratios on the stability of the dried bacteria. Results suggested that optimal molar ratio between the glass enhancers and the carbohydrates mixture is about 0.12-0.15.

Example 7

Effect of the Composition of the Current Invention on Storage Stability of the Probiotic Bacteria *L. acidophilus*

Figure 3:
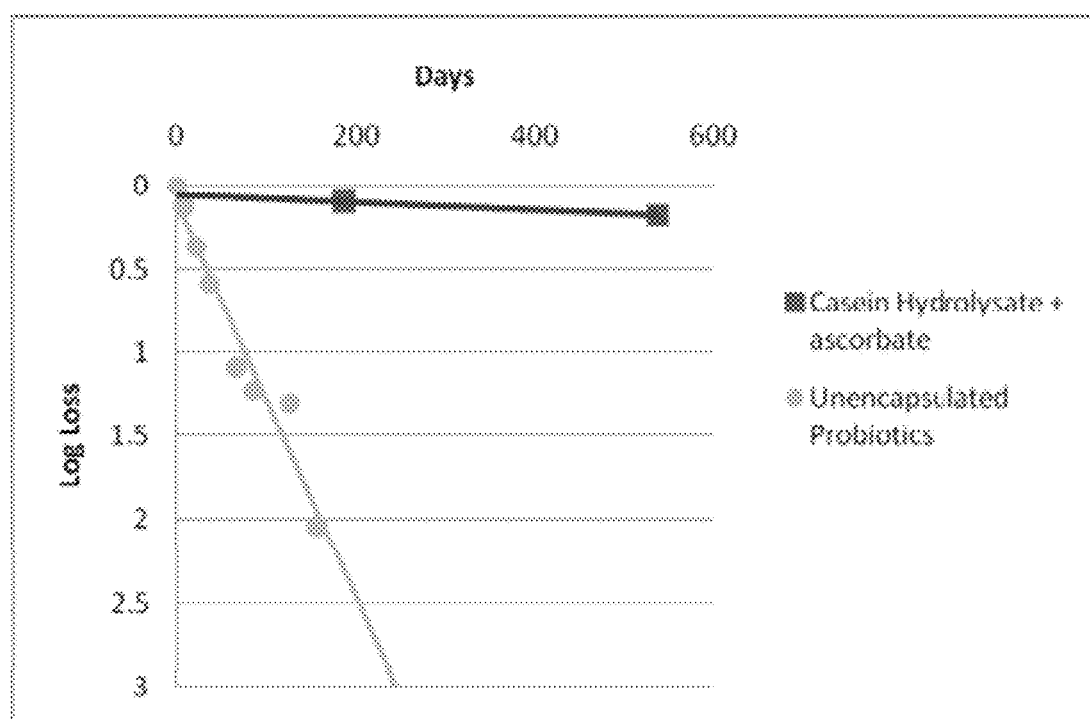
FIG. 3 shows the effect of the composition of the current invention on storage stability of the probiotic bacteria *L. acidophilus*. The stability of the dry probiotic bacteria was tested at accelerated storage conditions of 24° C. and 33% RH for 537 days.

A composition containing carbohydrates mixture and glass enhancers mixture as described in Example 1 was prepared. A concentrated culture of the probiotic bacteria *L. acidophilus* was obtained from a commercial source and prepared in a dry composition as described in Examples 1 and 3 and the stable powder was subjected to acceleration storage conditions at 24° C. and 33% RH for 537 days. FIG. 3 demonstrates the superior stability of the probiotic formulated with the composition of the current invention. Results show that the probiotic viability reduced by only 0.18 log over 537 days of shelf storage under the specified conditions.

Example 8

Effect of Various Glass Enhancers Compounds on Storage Stability of the Probiotic Bacteria *L. Acidophilus*.

Figure 4:
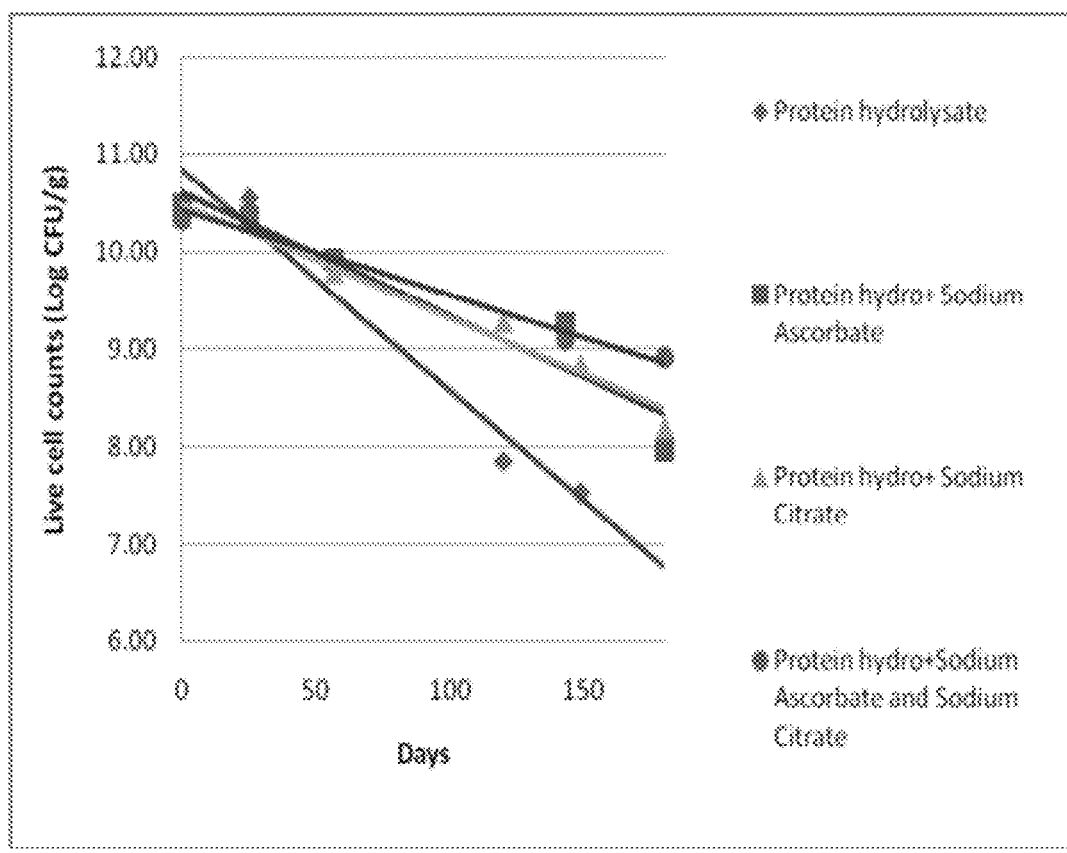
FIG. 4 shows the effect of various glass enhancers compounds on storage stability of the probiotic bacteria *L. acidophilus*. The stability of the dry probiotic bacteria was tested at accelerated storage conditions of 24° C. and 43% RH for 180 days.

Several composition containing carbohydrates mixture as described in Example 1 and glass enhancers mixture containing casein hydrolysate and sodium citrate or sodium ascorbate or a combination of both were prepared. A concentrated culture of the probiotic bacteria *L. acidophilus* was obtained from a commercial source and prepared in a dry composition as described in Example 1 except that the slurry was immediately loaded on trays in wet form without snap-freezing and purging steps. The slurry was dried in primary and secondary stages as described in Examples 1 and 3 and the stable powder was subjected to acceleration storage conditions at 24° C. and 43% RH for 180 days. FIG. 4 show the effect of various glass enhancing compounds on the stability of the dried bacteria. Results suggested that a significant better stability was obtained by the inclusion of additional glass enhancer on top of the protein hydrolysate. In particular, the inclusion of equal amounts of sodium acetate and sodium ascorbate provided the most stable composition. Results from both Examples 5 and 6 also suggested that various glass enhancers may be more effective or even may act as a destabilize depending on the bacterial strain.

Example 9

Effect of Various Protein Hydrolysate/Sugar Ratios on Storage Stability of the Probiotic Bacteria *Bifidobacterium Lactis*.

Figure 5:
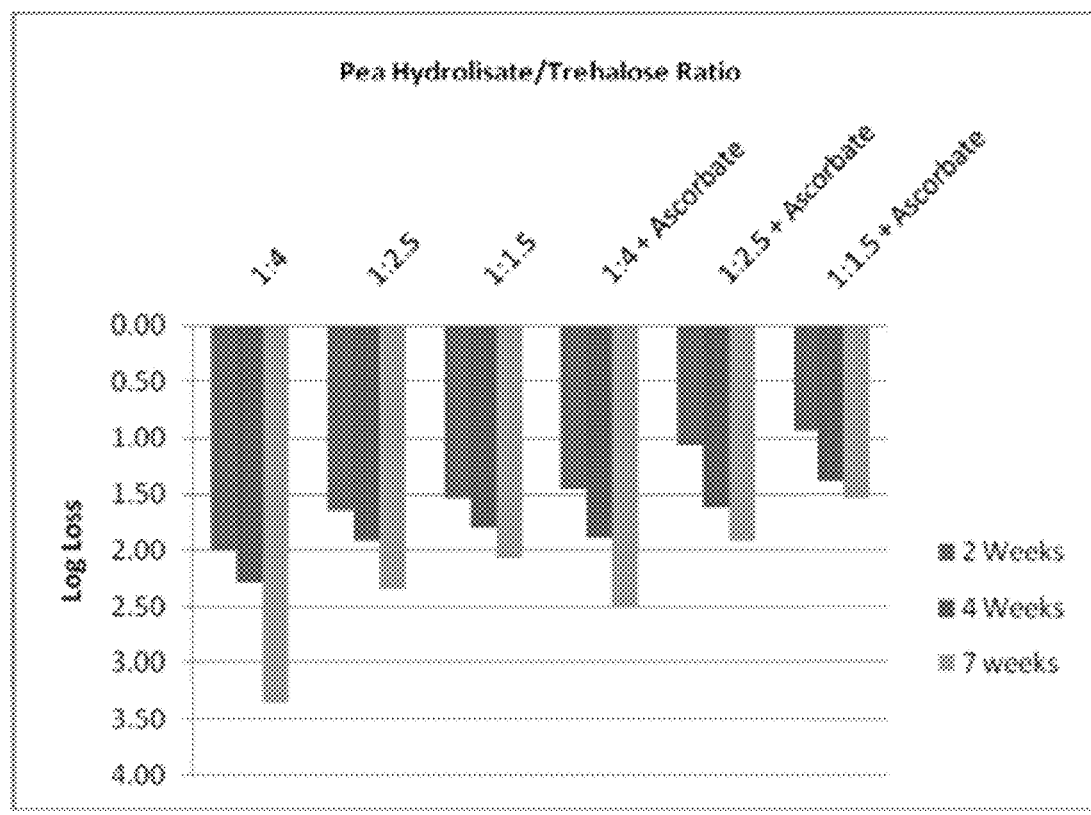
FIG. 5 shows the effect of various protein hydrolysate/sugar ratios on storage stability (35° C. and 43% RH) of the probiotic bacteria *Bifidobacterium lactis*.

Several compositions containing carbohydrates mixture and glass enhancers as described in Example 1 and compositions containing equal amounts but at various ratios of pea hydrolysate/trehalose with or without sodium ascorbate were prepared. A concentrated culture of the probiotic bacteria *Bifidobacterium lactis* was obtained from a commercial source and prepared in a dry composition as described in Examples 1 and 3 and the stable powder was subjected to acceleration storage conditions at 35° C. and 43% RH for 7 weeks. FIG. 5 show the effect of 1:4, 1:2.5 and 1:1.5 ratios of pea hydrolysate/trehalose with or without sodium ascorbate on the stability of the dried bacteria. Results suggested that a significant better stability was obtained at increasing ratios of pea hydrolysate/trehalose. In particular, a ratio of 1:1.5 pea hydrolysate/trehalose provided more stable composition. Inclusion of sodium ascorbate at higher pea hydrolysate/trehalose ratio resulted in superior stability compared to sodium ascorbate excluded formulations.

Example 10 pH Optimization for Maximum Stability of the Probiotic *L. Rhamnosus*.

Figure 6:
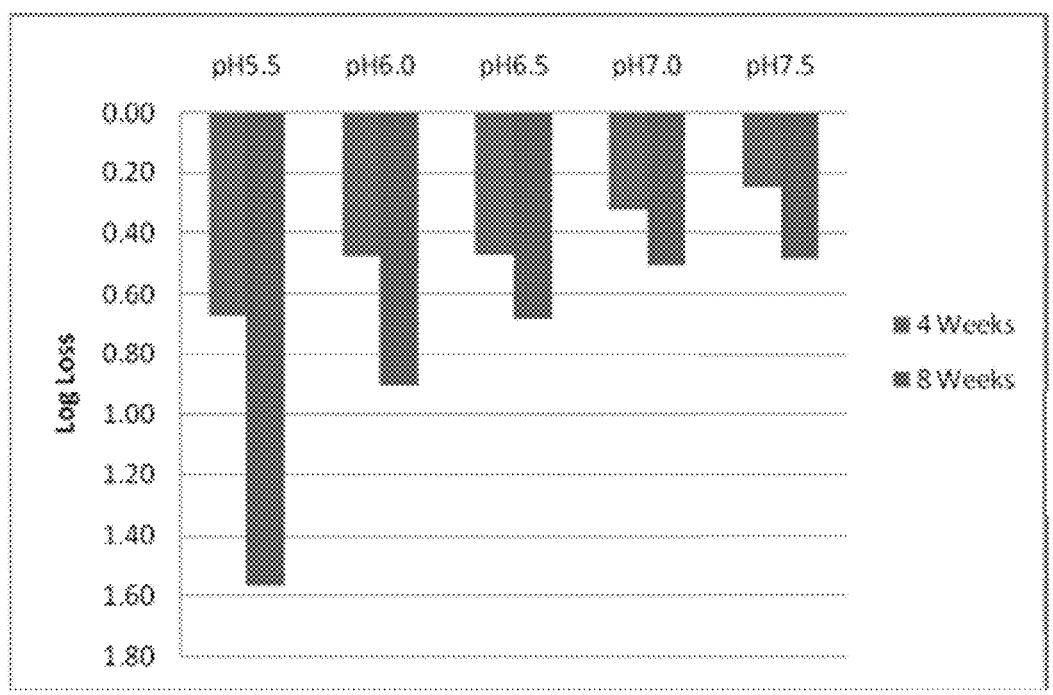
FIG. 6 shows pH optimization for maximum stability of the probiotic *L. rhamnosus* (acceleration storage conditions at 40° C. and 33% RH for 8 weeks).

Several compositions containing carbohydrates mixture and glass enhancers as described in Example 1 at different pHs were prepared. A concentrated culture of the probiotic bacteria *L. rhamnosus* was obtained from a commercial source and prepared in a dry composition as described in Examples 1 and 3. The stable powder was subjected to acceleration storage conditions at 40° C. and 33% RH for 8 weeks. FIG. 6 show the pH effect of the slurry on the stability of the dried bacteria. Results suggested that optimal stability was achieved at neutral pH (~7).

Example 11

Stable Dry Powder Containing an Enzyme:

A hydrogel formula containing 40 weight percent of phitase (BASF, GmBH) is prepared by mixing 400 g of the carbohydrates mixture and 200 g of the glass enhancers mixture as described in Examples 1 and 4 and 400 g of phitase in 1000 ml of water. The shredded hydrogel formulation is snap-frozen in liquid nitrogen and dried in a vacuum oven at a primary and secondary drying temperature of 50° C. For determination of loading and storage stability of the dried formula: a dry sample is accurately weighed (<100 mg) in a microcentrifuge tube. 200 µl of dimethyl sulfoxide (DMSO) is added. The formulation is dissolved in the DMSO buffer by vortexing. To this sample, 0.8 ml of a solution containing 0.05 N NaOH, 0.5% SDS and 0.075 M Citric acid (trisodium salt) is added. The tubes are sonicated for 10 min at 45° C., followed by a brief centrifugation at 5,000 rpm for 10 min. Aliquots of the clear DMSO/NaOH/SDS/Citrate solution are taken into wells of a microplate and analyzed for protein content using the Bradford assay method. The stability of the stable enzyme dry composition after exposure to 95° C. for 20 min is significantly higher than a dry enzyme without the composition of the present invention.

Example 12

Stable Dry Powder Containing an Infectious Salmon Anemia Virus (ISAV) Vaccine

Concentrated slurry of ISAV vaccine (Novozyme, Denmark) is prepared according to Example 4 except that 20 ml 4% chitosan solution in 0.5% acetic acid was added to the slurry containing the ISAV vaccine concentrate, the carbohydrates mixture and the glass enhancers. 0.5 g of dibasic calcium phosphate is added, followed by 0.5 g of gluconolactone. The slurry is allowed to harden at room temperature over the next 2 hours to form a solid hydrogel. The firm gel is sliced to thin and long threads, using a commercially available slicer/shredder. The thin threads are directly loaded on trays in wet form or snap-frozen in liquid nitrogen and loaded on a tray at a loading capacity of 1500 g/sq ft and placed in a freeze drier for drying as described in Example 3. The water activity (Aw) of the formulation is 0.25. The dry formulation is further ground to fine powder using standard hammer milling equipment and sieved through 50-150 micron screens. The stable dry ISAV composition is used for oral vaccination by top coating a commercial feed with the dry composition and feeding to Atlantic salmon fish.

Example 13

Preparation of Invasive Species Bait

Pelleted bait for specifically targeted invasive species according to the present invention is prepared containing a pesticide. 200 g of a formulation as described in Example 9 is prepared and added to 200 gm of water. To this solution is added 90 gm of Rotenone and 0.5 gm of calcium phosphate dibasic, followed by 0.5 gm of gluconolactone. The slurry is immediately spray dried in a standard industrial pray drier, and the dry formulation is used for targeting specific invasive species without deleterious effect of the toxin on the environment or close-by ecosystems.

Example 14

Preparation of a Protected Plant Probiotic Formulation:

A biological control agent such as *Rhizobacteria* is prepared in dry composition according to Example 4. The effectiveness of the dry *Rhizobacteria* composition is evaluated on lettuce growth under gnotobiotic conditions. Doses of 100 mg of *Rhizobacteria* dry composition per plant are inoculated into jars with sand and planted with pre-germinated (24 h) lettuce seedlings. A nutrient dose of 5 ml of sterilized Hoagland solution is applied to the plants in the jar. Jars are arranged randomly in growth chamber maintained at 28° C. with 12 h photoperiod. During every 7 days interval after inoculation, plants and adhering sand are carefully removed from the jars. Roots are washed in sterile phosphate buffer (pH 7.0), and measurement of root length is recorded.

REFERENCES

The contents of the following references are hereby incorporated by reference herein for all purposes.

U.S. Patent and Patent Application References:

U.S. Pat. No. 6,190,701 Composition and method for stable injectable liquids, March 1999, Roser et al.

U.S. Pat. No. 6,964,771 Method for stably incorporating substances within dry, foamed glass matrices, September 1997, Roser et al.

U.S. Pat. No. 5,766,520 Preservation by formulation formation, June 1998, Bronshtein.

U.S. Pat. No. 6,534,087 Process for preparing a pharmaceutical composition, June 2001, Busson and Schroeder.

U.S. Pat. No. 6,884,866 Bulk drying and the effects of inducing bubble nucleation, April 2005, Bronshtein.

U.S. Pat. No. 7,153,472 Preservation and formulation of bioactive materials for storage and delivery in hydrophobic carriers, December, 2006, Bronshtein.

2008/0229609, Preservation by Vaporization., June 2005, Bronshtein.

U.S. Pat. No. 6,306,345 Industrial scale barrier technology for preservation of sensitive biological materials at ambient temperatures, October 2001, Bronshtein et al.

U.S. Pat. No. 7,381, 425, Preservation of bioactive materials by freeze dried foam, September 2006, Truong-le, Vu.

OTHER REFERENCES:

Morgan, C. A., Herman, N., White, P. A., Vesey, G., 2006, Preservation of micro-organisms by drying; a review. *J. Microbiol. Methods.* 66(2):183-93.

Capela, P., Hay, T. K. C., & Shah, N. P., 2006, Effect of cryoprotectants, prebiotics and microencapsulation on survival of probiotic organisms in yoghurt and freeze-dried yoghurt. *Food Research International,* 39(3) 203-211).

Annear, 1962, The Preservation of *Leptospires* by Drying From the Liquid State, *J. Gen. Microbiol.,* 27:341-343.

Crowe, J. F., Carpenter, J. F. and Crowe, L. M., 1998, THE ROLE OF VITRIFICATION IN ANHYDROBIOSIS. *Annu. Rev. Physiol.* 60:73-103.

Crowe, J. H., Crowe., L. M., and Mouriadian, R., 1983, *Cryobiology,* 20, 346-356.

M. Le Meste, et al., 2002, Glass Transition and Food Technology: A Critical Appraisal, *Journal of Food Science*, 67:2444-2458.

Sanchez et al., 1999, *Intl. J. Pharm.* 185, 255-266.

Esquisabel et al., 1997, *J. Microencapsulation*, 14, 627-638.

Kets et al., 2004. Citrate increases glass transition temperature of vitrified sucrose preparations, *Cryobiology*, 48:46-54.

That which is claimed is:

1. A dry glassy stabilizing composition, comprising a bioactive material, one or more disaccharides at 10-90%, one or more oligosaccharides at 1-10%, one or more polysaccharides at 0.1-10%, one or more hydrolyzed proteins at 0.5-40%, and one or more carboxylic acid salts, each percentage based on the total weight of the composition, wherein the one or more carboxylic acid salts are selected from the group consisting of salts of lactic acid, ascorbic acid, maleic acid, oxalic acid, malonic acid, malic acid, succinic acid, citric acid, gluconic acid, glutamic acid, and a mixture thereof, and wherein the bioactive material consists of a live microorganism.

2. The composition of claim 1, wherein the one or more disaccharides are present at 40-80%, the one or more oligosaccharides are present at 5-10%, and the one or more polysaccharides are present at 5-10%, each percentage based on the total weight of the composition.

3. The composition of claim 1, wherein the one or more hydrolyzed proteins are selected from the group consisting of hydrolyzed casein, hydrolyzed whey protein, hydrolyzed pea protein, hydrolyzed soy protein and a mixture thereof, and wherein each of the one or more hydrolyzed proteins has a molecular weight of from 1 kDa to 50 kDa.

4. The composition of claim 1, wherein the one or more polysaccharides comprise cellulose acetate phthalate (CAP), carboxymethyl cellulose, pectin, sodium alginate, salts of alginic acid, hydroxypropyl methyl cellulose (HPMC), methyl cellulose, carrageenan, gellan gum, guar gum, gum acacia, xanthan gum, locust bean gum, chitosan, chitosan derivatives, collagen, polyglycolic acid, starches, modified starches, or a mixture thereof; wherein the one or more oligosaccharides comprise cyclodextrins, inulin, maltodextrins, dextrans, fructo-oligosaccharides (FOS), galacto-oligosaccharides (GOS), mannan-oligosaccharides (MOS), or a mixture thereof; and wherein the one or more disaccharides comprise trehalose, sucrose, lactose, or a mixture thereof.

5. The composition of claim 1, wherein the one or more carboxylic acid salts comprise a salt of ascorbic acid, and wherein the molar ratio of ascorbate ions to a combination of the one or more disaccharides, the one or more oligosaccharides, and the one or more polysaccharides is from 0.01 to 0.3.

6. The composition of claim 1, wherein the weight ratio of disaccharides/oligosaccharides/polysaccharides is from 10:0.2:0.1 to 10:2:1.

7. A method for preparing a dry glassy stabilizing composition comprising a biological material, one or more disaccharides at 10-90%, one or more oligosaccharides at 1-10%, one or more polysaccharides at 0.1-10%, one or more hydrolyzed proteins at 0.5-40%, and one or more carboxylic acid salts, each percentage based on the total weight of the composition, wherein the one or more carboxylic acid salts are selected from the group consisting of salts of lactic acid, ascorbic acid, maleic acid, oxalic acid, malonic acid, malic acid, succinic acid, citric acid, gluconic acid, glutamic acid, and a mixture thereof, wherein the bioactive material consists of a live microorganism, comprising: (a) combining the bioactive material with the one or more disaccharides, the one or more oligosaccharides, the one or more polysaccharides, the one or more hydrolyzed proteins, and the one or more carboxylic acid salts in an aqueous solvent to form a slurry;

(b) snap-freezing the slurry in liquid nitrogen to form solid frozen particles in a form of beads, droplets or strings;

(c) primary drying the frozen particles by evaporation under vacuum and at a temperature above the freezing temperature of the frozen particles to form a primarily dried formulation; and (d) secondary drying the primarily dried formulation at higher vacuum and at a temperature of 20° C. or higher for a time sufficient to reduce the water activity thereof; whereby the dry stabilizing composition is obtained.

8. The method of claim 7, further comprising a temperature acclimation step of the solid frozen particles before initiating the primary drying step.

9. The method of claim 7, wherein the viscous slurry is solidified to a firm hydrogel by a pH or temperature change or by cross linking before the snap freezing.

10. The method of claim 8, wherein the acclimation step is carried out under vacuum and at a temperature below the freezing point of the solid frozen particles.

11. The method of claim 7, wherein the primary liquid drying step is carried out at a pressure higher than 2000 mTORR.

12. The method of claim 7, further comprising cutting, crushing, milling or pulverizing the composition of step (d) into a free flowing powder.

13. The method of claim 12, wherein the free flowing powder has a particle size less than 1000 μm.

14. The method of claim 7, wherein the water activity (Aw) of the dry glassy stabilizing composition is less than 0.3.

15. A product prepared from the dry glassy stabilizing composition of claim 1, wherein the product is an oral delivery formulation in the form of a reconstituted liquid, a ground powder, a tablet, a pellet, a capsule, a food or a feed product.

16. A product comprising the dry glassy stabilizing composition of claim 1, wherein the product is a food, a food additive, an animal feed, an animal feed additive, or a nutraceutical, pharmaceutical or vaccine product.

17. The product of claim 16, wherein the product is in the form of a bar, liquid formula, colloidal suspension, powder, tablet or capsule.

18. The composition of claim 1, wherein the bioactive material is embedded in the dry glassy stabilizing composition.

19. The composition of claim 1, wherein the one or more hydrolyzed proteins comprise pea protein hydrolysate.

20. The composition of claim 1, wherein the one or more carboxylic acid salts are present in a range from 0.5% to 20% by weight of the composition.

21. The composition of claim 1, wherein the one or more carboxylic acid salts comprise a salt of ascorbic acid.

22. The method of claim 7, wherein the one or more carboxylic acid salts comprise a salt of ascorbic acid.

23. A dry glassy stabilizing composition obtained by the method of claim 7.

24. A dry glassy stabilizing composition obtained by the method of claim 22.

* * * * *